United States Patent
Dudee et al.

(10) Patent No.: US 10,265,163 B2
(45) Date of Patent: Apr. 23, 2019

(54) ACCOMMODATING INTRAOCULAR LENS ASSEMBLY

(71) Applicants: Jitander Dudee, Lexington, KY (US); Serena Helen Dudee, Lexington, KY (US)

(72) Inventors: Jitander Dudee, Lexington, KY (US); Serena Helen Dudee, Lexington, KY (US)

(*) Notice: Subject to any disclaimer, the term of this patent is extended or adjusted under 35 U.S.C. 154(b) by 121 days.

(21) Appl. No.: 14/979,449

(22) Filed: Dec. 27, 2015

(65) Prior Publication Data
US 2016/0184089 A1    Jun. 30, 2016

Related U.S. Application Data

(60) Provisional application No. 62/097,052, filed on Dec. 27, 2014.

(51) Int. Cl.
*A61F 2/16* (2006.01)

(52) U.S. Cl.
CPC ............ *A61F 2/1632* (2013.01); *A61F 2/161* (2015.04); *A61F 2/1602* (2013.01);
(Continued)

(58) Field of Classification Search
CPC .. A61F 2/1632; A61F 2/16015; A61F 2/1608; A61F 2/1602; A61F 2/1629;
(Continued)

(56) References Cited

U.S. PATENT DOCUMENTS

| 4,685,922 A | 8/1987 | Peyman |
| 4,950,289 A | 8/1990 | Krasner |

(Continued)

FOREIGN PATENT DOCUMENTS

| CN | 1087505 A | 6/1994 |
| EP | 0949529 A2 | 10/1999 |

(Continued)

OTHER PUBLICATIONS

Hara et al., Accommodative Intraocular Lens with Spring Action, Sep. 1992, Ophthalmic Surgery, vol. 23, 632-635.*

(Continued)

*Primary Examiner* — David H Willse
*Assistant Examiner* — Tiffany P Shipmon
(74) *Attorney, Agent, or Firm* — Black, McCuskey, Souers & Arbaugh, LPA

(57) ABSTRACT

A method of positioning an accommodating intraocular lens assembly in an eye can include implanting an accommodating intraocular lens assembly having a positive power lens in the eye. The accommodating intraocular lens assembly can also include a plurality of stanchions extending between base ends and distal ends. The base ends can be disposed in spaced relation to one another about a first arcuate periphery positioned in a ciliary sulcus of the eye. The distal ends can be disposed about a second arcuate periphery extending in a second plane positioned forward and outside of a capsular bag of the eye. The positive-power lens can be connected with the plurality of distal ends whereby a center of the positive power lens is moved along the central optic axis in response to contraction of the first arcuate periphery by contraction of the ciliary sulcus.

20 Claims, 22 Drawing Sheets

(52) U.S. Cl.
CPC ........ *A61F 2/1608* (2015.04); *A61F 2/16015* (2015.04); *A61F 2/1629* (2013.01); *A61F 2/1648* (2013.01); *A61F 2002/1682* (2015.04); *A61F 2002/1683* (2013.01)

(58) Field of Classification Search
CPC .................. A61F 2/1624; A61F 2/1613; A61F 2002/1681; A61F 2002/1682; A61F 2002/1683; A61F 2002/1686; G02C 7/083
See application file for complete search history.

(56) References Cited

U.S. PATENT DOCUMENTS

| | | | |
|---|---|---|---|
| 5,725,575 | A | 3/1998 | O'Donnell, Jr. |
| 5,728,155 | A | 3/1998 | Anello et al. |
| 6,013,101 | A * | 1/2000 | Israel .................... A61F 2/1629 623/6.43 |
| 6,767,363 | B1 | 7/2004 | Bandhauer et al. |
| 7,591,849 | B2 | 9/2009 | Richardson |
| 8,062,361 | B2 | 11/2011 | Nguyen et al. |
| 8,109,998 | B2 | 2/2012 | Cumming |
| 8,182,531 | B2 | 5/2012 | Hermans et al. |
| 8,343,216 | B2 | 1/2013 | Brady et al. |
| 8,382,831 | B2 | 2/2013 | Ben Nun |
| 8,425,597 | B2 | 4/2013 | Glick et al. |
| 8,496,701 | B2 | 7/2013 | Hermans et al. |
| 8,734,512 | B2 | 5/2014 | Cumming |
| 8,834,565 | B2 | 9/2014 | Ben Nun |
| 8,920,495 | B2 | 12/2014 | Mirlay |
| 9,005,283 | B2 | 4/2015 | Nguyen et al. |
| 9,011,532 | B2 | 4/2015 | Bumbalough et al. |
| 9,039,760 | B2 | 5/2015 | Brady et al. |
| 9,125,736 | B2 | 9/2015 | Kahook et al. |
| 2003/0060881 | A1 | 3/2003 | Glick et al. |
| 2004/0010310 | A1 | 1/2004 | Peyman |
| 2005/0027354 | A1 | 2/2005 | Brady et al. |
| 2005/0113914 | A1 * | 5/2005 | Miller .................... A61F 2/1613 623/6.34 |
| 2006/0116764 | A1 | 6/2006 | Simpson |
| 2006/0184244 | A1 | 8/2006 | Nguyen et al. |
| 2006/0271186 | A1 | 11/2006 | Nishi et al. |
| 2008/0103592 | A1 | 5/2008 | Maloney |
| 2008/0288066 | A1 | 11/2008 | Cumming |
| 2010/0016965 | A1 | 1/2010 | Hong et al. |
| 2010/0152848 | A1 | 6/2010 | Williamson et al. |
| 2010/0179653 | A1 | 7/2010 | Argento et al. |
| 2011/0071628 | A1 | 3/2011 | Gross et al. |
| 2011/0098812 | A1 | 4/2011 | Ben Nun |
| 2011/0307058 | A1 | 12/2011 | Beer |
| 2012/0203239 | A1 | 8/2012 | Vukich et al. |
| 2012/0310343 | A1 | 12/2012 | Van Noy |
| 2013/0041382 | A1 | 2/2013 | Ben Nun |
| 2013/0110234 | A1 | 5/2013 | DeVita et al. |
| 2013/0116781 | A1 | 5/2013 | Ben Nun |
| 2013/0131794 | A1 | 5/2013 | Smiley et al. |
| 2013/0304203 | A1 | 11/2013 | Beer |
| 2014/0257478 | A1 * | 9/2014 | McCafferty ........... A61F 2/1629 623/6.13 |
| 2014/0257480 | A1 | 9/2014 | Van Der Mooren et al. |
| 2015/0105760 | A1 | 4/2015 | Rao et al. |
| 2015/0142108 | A1 * | 5/2015 | Akura ................... A61F 2/1624 623/6.37 |

FOREIGN PATENT DOCUMENTS

| | | |
|---|---|---|
| WO | 2004006809 A1 | 1/2004 |
| WO | 2008031006 A2 | 3/2008 |
| WO | 2013166068 A1 | 11/2013 |

OTHER PUBLICATIONS

Donnenfeld, Eric D., MD, "An Autofocal Accommodating IOL: The Sapphire implant is the first to allow visual accommodation without movement of the lens," Cataract & Refractive Surgery Today Europe, Jan. 2015, pp. 44-45.

Duane, Alexander, MD, "Studies in monocular and binocular accommodation, with their clinical application," Trans Am Ophthalmol Soc. 1922; 20: 132-157.

Goldberg, Daniel B., MD, "Computer-animated model of accommodation and bresbyopia," J Cataract Refract Surg 2015; 41:437-445.

Kohnen, Thomas, MD, PhD, FEBO, "Objective measurement of accommodation," J Cataract Refract Surg—vol. 41, Mar. 2015, From the Editor.

Marchini, et al. "Anterior segment changes during accommodation in eyes with a monofocal intraocular lens: High-frequency ultrasound study," J Cataract Refract Surg 2008; 34:949-956.

Ostrin et al., "Accommodation measurements in a prepresbyopic and presbyopic population," J Cataract Refract Surg 2004; 30:1435-1444.

Ramasubramanian, Viswanathan, PhD, et al., "Objective measurement of accommodative biometric changes using ultrasound biomicroscopy," J Cataract Refract Surg 2015; 41:511-526.

\* cited by examiner

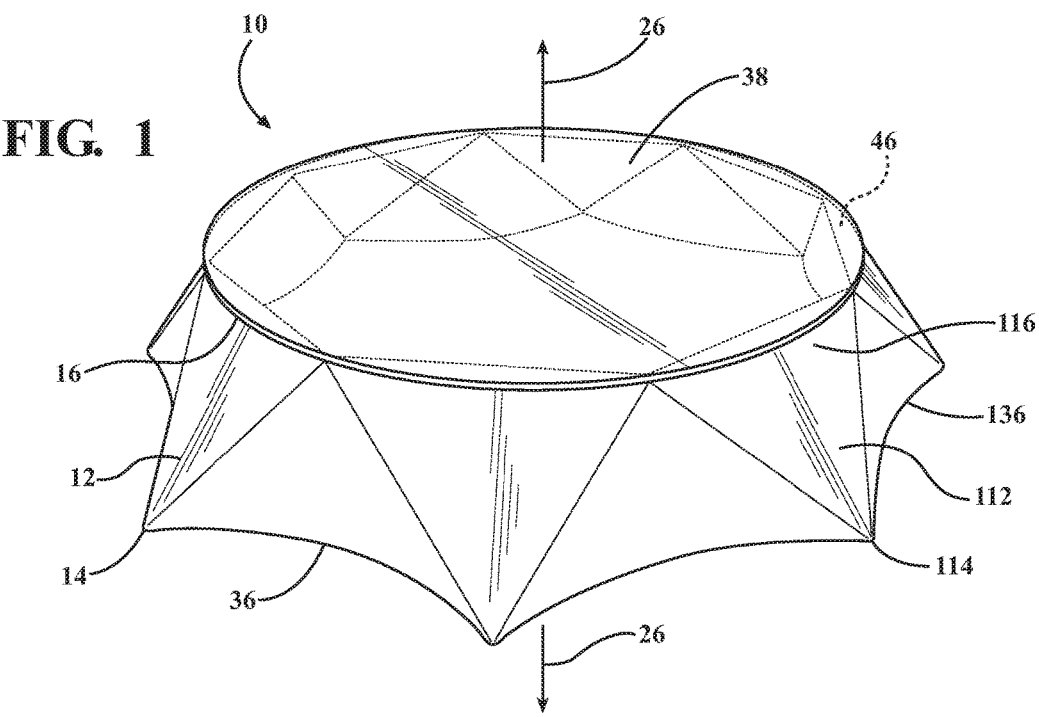
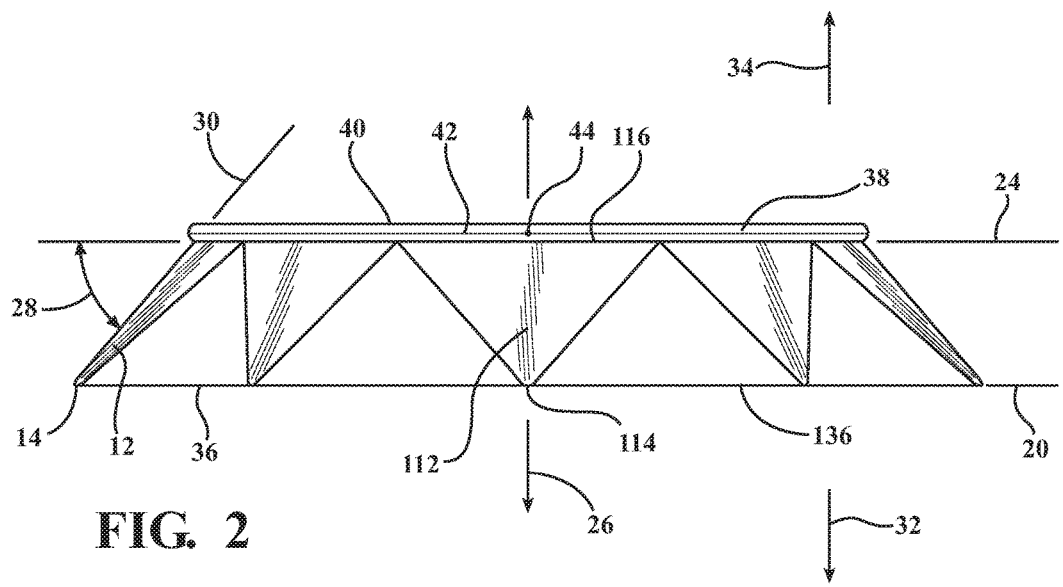

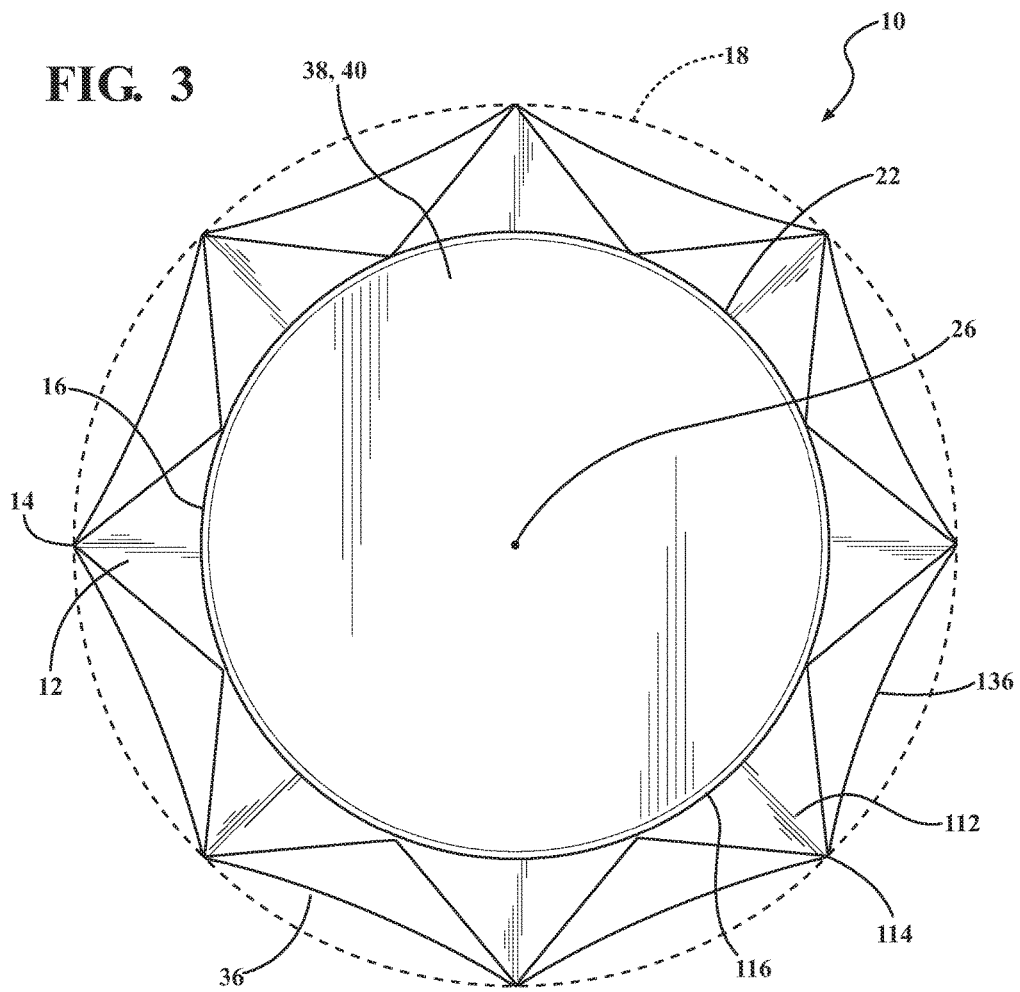

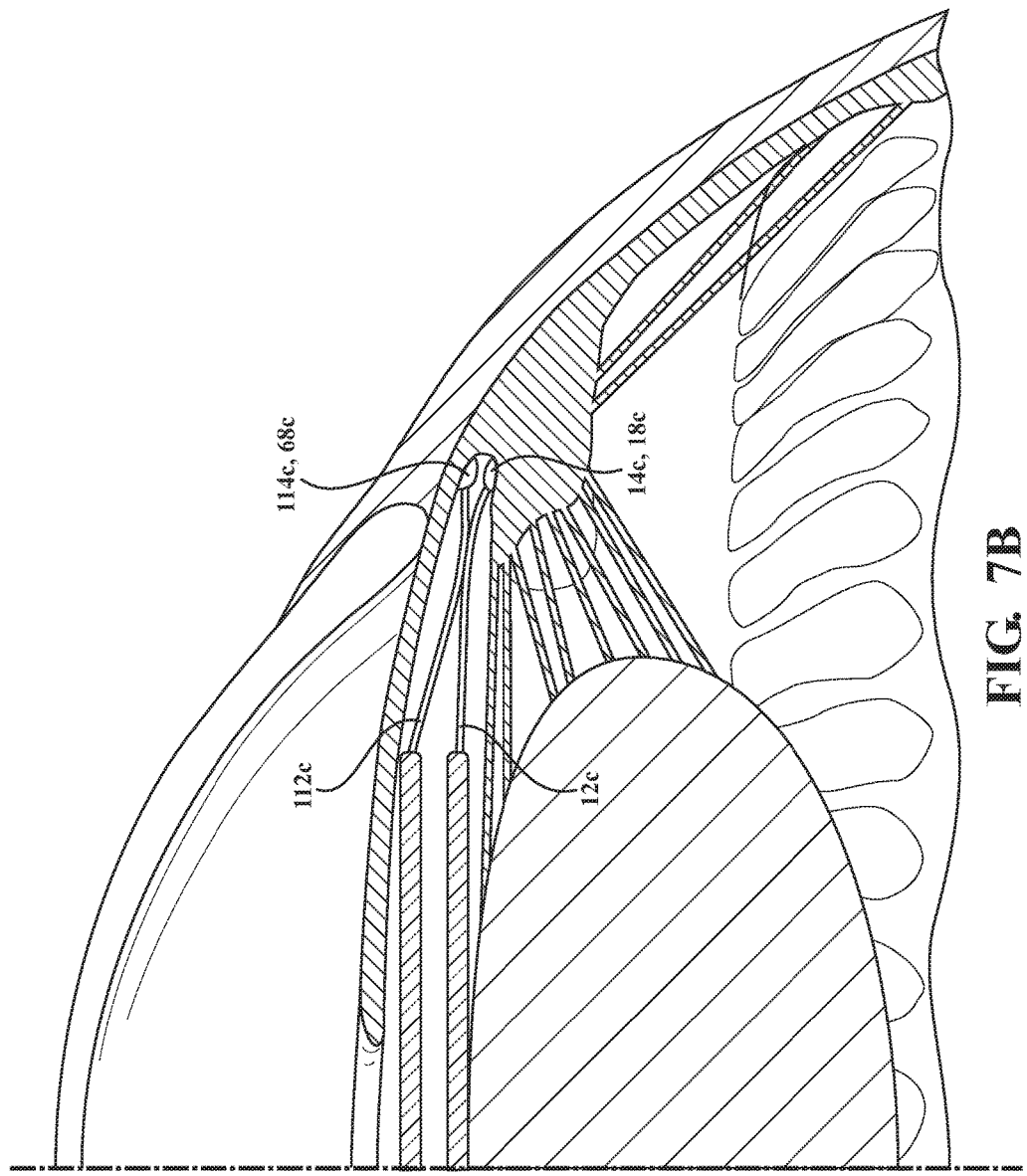

ACCOMMODATING INTRAOCULAR LENS ASSEMBLY

CROSS-REFERENCE TO RELATED APPLICATIONS

This application claims the benefit of U.S. Provisional Patent Application Ser. No. 62/097,052 for a POST SURGERY MODIFIABLE DYNAMICALLY ACCOMMODATING INTRA-OCULAR LENS IMPLANT, filed on 27 Dec. 2014, which is hereby incorporated by reference in its entirety.

BACKGROUND

1. Field

The present disclosure relates to structures positionable in a human eye such as intraocular lens arrangements, drug delivery systems, sensor holders, and glaucoma treatment devices.

2. Description of Related Prior Art

Prosthetic intra-ocular lenses (IOLs) are routinely implanted following cataract extraction in human eyes and have grown in sophistication in order to provide better functional visual acuity with fewer troublesome distortions, reflections and aberrations to images focused on the retina. However, the natural lens retains distinct advantages over currently available IOLs. One such quality is the ability to alter its optical power to allow clear focusing on near as well as distant objects through human volition in tandem with contraction of the ciliary muscle of the eye. The physiological mechanism whereby the human eye voluntarily alters its focal point from distance to near is termed "near-accommodation" and a prosthetic lens implant that seeks to perform this function is termed an Accommodating IOL or AIOL. Several designs have been proposed in the prior art for AIOLS that attempt to achieve the variable focus distance of the youthful natural lens but all have significant limitations.

U.S. Pat. Pub. No. 2005/0027354 discloses a PRIMARY AND SUPPLEMENTAL INTRAOCULAR LENS. The intraocular lens system includes a primary intraocular lens configured to correct vision in a patient, and a supplemental intraocular lens configured to modify the correction provided by the primary intraocular lens. The supplemental intraocular lens, which is substantially completely diffractive, is preferably ultrathin. The two lenses may be connected to, or separate from, one another. The supplemental intraocular lens may be implanted at the same time as the primary intraocular lens, or added later.

U.S. Pat. Pub. No. 2008/0288066 discloses a TORIC SULCUS LENS. There is disclosed therein a "piggyback" cylindrical (toric) intraocular lens for placement in front of an accommodating or standard intraocular lens that is already in the capsular bag of the eye. This additional lens is placed in the sulcus, which leaves a significant space between the two lenses, particularly if the lens in the capsular bag is vaulted backwards.

U.S. Pat. No. 8,425,597 discloses ACCOMMODATING INTRAOCULAR LENSES. Intraocular lenses for providing accommodation include an anterior optic, a posterior optic, and a lens structure. In one such lens, the lens structure comprises an anterior element coupled to the anterior optic and a posterior element coupled to the posterior optic. The anterior and posterior elements are coupled to one another at a peripheral region of the intraocular lens. The intraocular lens may also includes a projection extending anteriorly from the posterior element that limits posterior motion of the anterior optic so as to maintain a minimum separation between anterior optic and an anterior surface of the posterior optic.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

An accommodating intraocular lens assembly can include a plurality of stanchions and a positive-power lens. The plurality of stanchions can each extend between a base end and a distal end. The plurality of base ends can be disposed in spaced relation to one another about a first arcuate periphery extending in a first plane. The distal ends can be disposed about a second arcuate periphery extending in a second plane. The first plane can be spaced from the second plane in a posterior direction along a central optic axis. The first arcuate periphery can have a greater radius than the second arcuate periphery. The positive-power lens can have an anterior side and a posterior side and a center disposed between the anterior side and the posterior side. The positive-power lens can be connected with each of the plurality of distal ends whereby the center of the positive power lens is moved along the central optic axis in response to contraction of the first arcuate periphery.

According to other features, the accommodating intraocular lens assembly can also include a ring member interposed between the positive power lens and each of the plurality of distal ends. The ring member can be discontinuous.

In other features, the accommodating intraocular lens assembly can include at least one arcuate linking member extending along the first arcuate periphery. The at least one arcuate linking member can interconnect an adjacent pair of first and second of the plurality of base ends. The at least one arcuate linking member can be configured to not prevent adjacent base ends from moving relative to each other. The accommodating intraocular lens assembly can be centered on the central optic axis and the at least one arcuate linking member can be convex relative to the axis. The at least one arcuate linking member can be further defined as a plurality of arcuate linking members each respectively interconnecting adjacent pairs of the plurality of base ends.

According to other features, at least one of the plurality of stanchions is wider at the distal end than at the base end. At least one of the plurality of stanchions can progressively increase in a first width between the base end and the distal end in a third plane transverse to the central optic axis and maintains a substantially constant second width in a fourth plane containing the central optic axis.

In other features, at least one of the plurality of stanchions can contain fluid.

According to additional features, the first arcuate periphery can be configured for positioning in a ciliary sulcus and each of the plurality of stanchions can extend away from the positive power lens in the posterior direction at an acute angle greater than forty-five degrees and less than ninety degrees. At least one of the plurality of stanchions can extend along an arcuate profile in a plane containing the central optic axis, the arcuate profile defined by at least one radius and at least one center of curvature. At least one of the plurality of stanchions can extend along the arcuate profile in the plane containing the central optic axis, the arcuate profile defined by more than one radius or more than one center of curvature.

According to other features, the accommodating intraocular lens assembly can also include a second plurality of stanchions each respectively extending between a second base end and a second distal end. Each of the plurality of second base ends can be disposed in spaced relation to one another about a third arcuate periphery extending in a third plane. The second distal ends can be disposed about a fourth arcuate periphery extending in a fourth plane. The third plane can be spaced from the third plane along the central optic axis. The third arcuate periphery can have a greater radius than the fourth arcuate periphery. The fourth plane can be spaced from the first plane and from the second plane along the central optic axis. The accommodating intraocular lens assembly can also include a secondary lens having a second anterior side and a second posterior side and a second center disposed between the second anterior side and the second posterior side. The second anterior side can confront the posterior side. The secondary lens can be connected with each of the second plurality of distal ends whereby the second center of the secondary lens can be moved along the central optic axis in response to contraction of the third periphery.

According to other features, at least some of the plurality of second base ends can be interconnected to one of the plurality of base ends at respective intersections positioned along the first arcuate periphery such that the first arcuate periphery and the third arcuate periphery are coplanar. At least one of the plurality of stanchions can extend along a first arcuate profile in a plane containing the central optic axis. The first arcuate profile can be defined by at least one first radius and at least one first center of curvature. At least one of the second plurality of stanchions can extend along a second arcuate profile in a plane containing the central optic axis. The second arcuate profile can be defined by at least one second radius and at least one second center of curvature. The first arcuate profile and the second arcuate profile can extend away from the respective base end and second base end in the same direction along the central optic axis.

In other features, at least one of the plurality of stanchions can extend along a first arcuate profile in a plane containing the central optic axis. The first arcuate profile can be defined by at least one first radius and at least one first center of curvature. At least one of the second plurality of stanchions can extend along a second arcuate profile in a plane containing the central optic axis. The second arcuate profile can be defined by at least one second radius and at least one second center of curvature. The first arcuate profile and the second arcuate profile can extend away from the respective base end and second base end toward one another along the central optic axis.

A method of positioning an accommodating intraocular lens assembly in an eye can include implanting an accommodating intraocular lens assembly having a positive power lens in the eye. The accommodating intraocular lens assembly can also include a plurality of stanchions each extending between the respective base end and a distal end. The plurality of base ends can be disposed in spaced relation to one another about a first arcuate periphery extending in a first plane. The first arcuate periphery can be positioned in a ciliary sulcus of the eye. The distal ends can be disposed about a second arcuate periphery extending in a second plane positioned forward and outside of a capsular bag of the eye. The first plane can be spaced from the second plane in a posterior direction along a central optic axis. The first arcuate periphery can have a greater radius than the second arcuate periphery. The positive-power lens can have an anterior side and a posterior side and a center disposed between the anterior side and the posterior side. The positive-power lens can be connected with each of the plurality of distal ends whereby a center of the positive power lens is moved along the central optic axis in response to contraction of the first arcuate periphery by contraction of the ciliary sulcus.

According to other features, the implanting can be defined as implanting the accommodating intraocular lens assembly having the positive power lens in the eye wherein the accommodating intraocular lens assembly also includes a second plurality of stanchions each respectively extending between a second base end and a second distal end. Each of the plurality of second base ends can be disposed in spaced relation to one another about the first arcuate periphery and can be interconnected to one of the plurality of base ends at respective intersections positioned along the first arcuate periphery. The second distal ends can be disposed about a third arcuate periphery extending in a third plane. The third plane can be spaced from the first plane and the second plane along the central optic axis. The first arcuate periphery can have a greater radius than the third arcuate periphery. The accommodating intraocular lens assembly can also include a secondary lens having a second anterior side and a second posterior side and a second center disposed between the second anterior side and the second posterior side. The second anterior side can confront the posterior side. The secondary lens can be connected with each of the second plurality of distal ends whereby the second center of the secondary lens is moved along the central optic axis in response to contraction of the first arcuate periphery by contraction of the ciliary sulcus.

In other features, the implanting can further include implanting a second plurality of stanchions the accommodating intraocular lens assembly in the ciliary sulcus. Each of the second plurality of stanchions can respectively extending between a second base end and a second distal end. Each of the plurality of second base ends can be disposed in spaced relation to one another about a third arcuate periphery in a third plane spaced from the first plane along the central optic axis. The second distal ends can be disposed about a fourth arcuate periphery extending in a fourth plane. The fourth plane can be spaced from the third plane along the central optic axis. The third arcuate periphery can have a greater radius than the fourth arcuate periphery. The accommodating intraocular lens assembly can also include a secondary lens having a second anterior side and a second posterior side and a second center disposed between the second anterior side and the second posterior side. The second anterior side can confront the posterior side. The secondary lens can be connected with each of the second plurality of distal ends whereby the second center of the secondary lens is moved along the central optic axis in response to contraction of the first arcuate periphery by contraction of the ciliary sulcus.

BRIEF DESCRIPTION OF THE DRAWINGS

The detailed description set forth below references the following drawings:

FIG. 1 is a perspective view of an accommodating intraocular lens assembly according to an exemplary embodiment of the present disclosure;

FIG. 2 is a side view of the exemplary embodiment of the present disclosure;

FIG. 3 is a top view of the exemplary embodiment of the present disclosure;

FIGS. 5A and 5B define split cross-sectional views showing the accommodating intraocular lens assembly according to a second exemplary embodiment of the present disclosure position in an eye, wherein FIG. 5A shows the ciliary muscle in the relaxed condition and FIG. 5B shows the ciliary muscle in the contracted condition;

FIGS. 6A and 6B define split cross-sectional views showing the accommodating intraocular lens assembly according to a third exemplary embodiment of the present disclosure position in an eye, wherein FIG. 6A shows the ciliary muscle in the relaxed condition and FIG. 6B shows the ciliary muscle in the contracted condition;

FIGS. 7A and 7B define split cross-sectional views showing the accommodating intraocular lens assembly according to a fourth exemplary embodiment of the present disclosure position in an eye, wherein FIG. 7A shows the ciliary muscle in the relaxed condition and FIG. 7B shows the ciliary muscle in the contracted condition;

FIGS. 9A and 9B define split cross-sectional views showing the accommodating intraocular lens assembly according to another exemplary embodiment of the present disclosure position in an eye, wherein FIG. 9A shows the ciliary muscle in the relaxed condition and FIG. 9B shows the ciliary muscle in the contracted condition;

DETAILED DESCRIPTION

Figure 4:
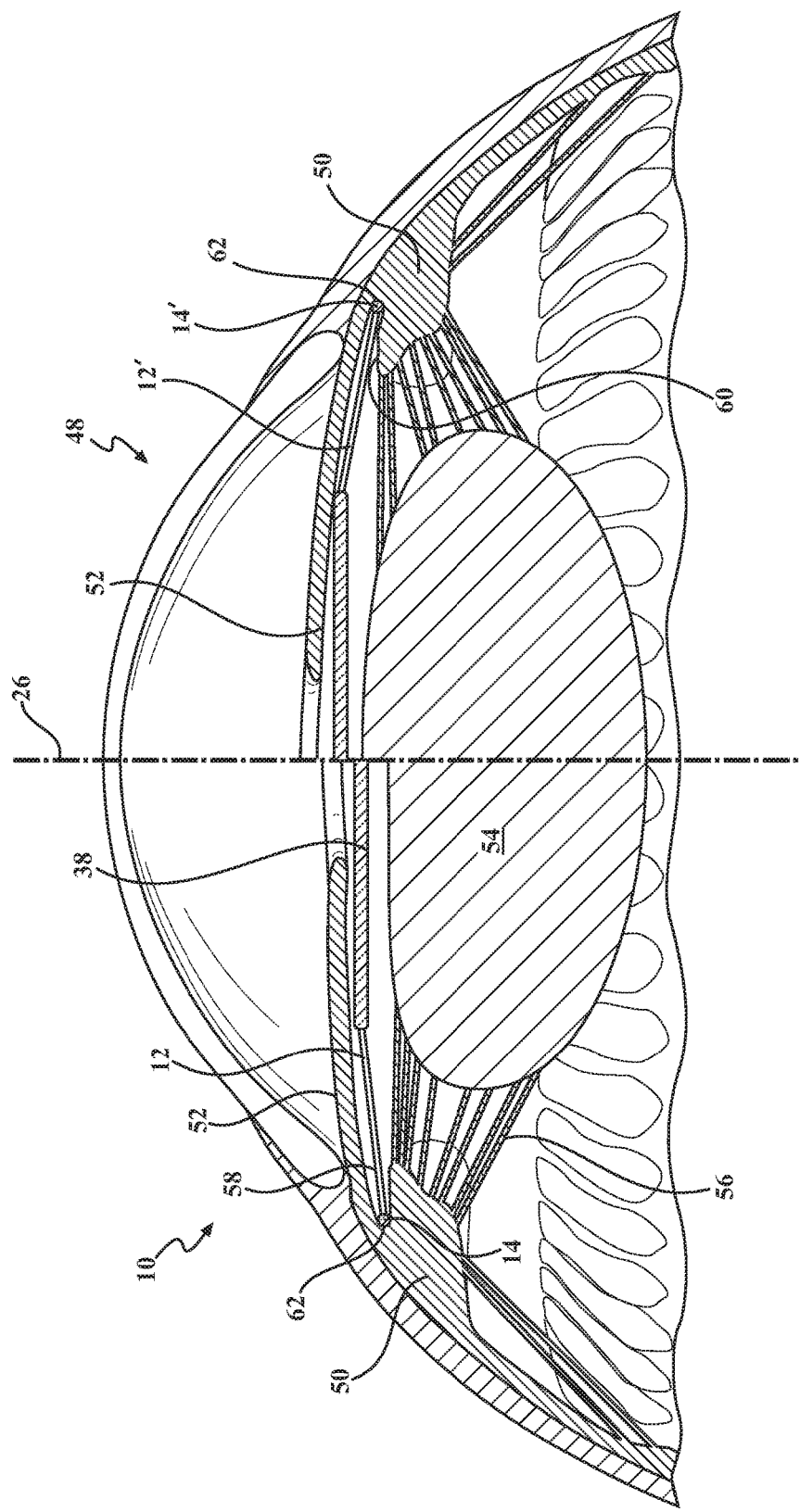
FIG. 4 is a split cross-sectional view showing the accommodating intraocular lens assembly according to the first exemplary embodiment of the present disclosure position in an eye, wherein the left side of the view shows the ciliary muscle in the relaxed condition and the right side of the view shows the ciliary muscle in the contracted condition.

A plurality of different embodiments of the present disclosure is shown in the Figures of the application. Similar features are shown in the various embodiments of the present disclosure. Similar features across different embodiments have been numbered with a common reference numeral and have been differentiated by an alphabetic suffix. Similar features in a particular embodiment have been numbered with a common two-digit, base reference numeral and have been differentiated by a different leading numeral. Also, to enhance consistency, the structures in any particular drawing share the same alphabetic suffix even if a particular feature is shown in less than all embodiments. Similar features are structured similarly, operate similarly, and/or have the same function unless otherwise indicated by the drawings or this specification. Furthermore, particular features of one embodiment can replace corresponding features in another embodiment or can supplement other embodiments unless otherwise indicated by the drawings or this specification.

The following terms are useful in the defining the operating environment of one or more embodiments of the present disclosure:

Intra-ocular Lens or "IOL" refers to a prosthetic optical lens placed within the eye to allow better visual functioning of the eye;

"Conventional IOL" refers to an IOL that has a single fixed focal point (also known as a monofocal IOL);

"Near Accommodation" or "Accommodation" refers to a change in the focal point of the optical system of the human eye from fixation on distant objects (those further away than about 6 meters from the eye) to near objects (those closer than about 0.5 meters from the eye), the term "accommodation" also includes the act of focusing on objects in the intermediate range of 6 to 0.5;

"Ciliary Body" or "CB" refers to the Ciliary Body of the eye including the various neuromuscular elements comprising the structure commonly referred to as the Ciliary Muscle, as well as the connective tissue joining the muscular elements and forming attachments of the ciliary muscle to the sclera and to the zonules or suspensory ligaments of the lens capsule. The muscular tissue within the CB is generally of the type known as "smooth muscle". Many microscopic muscle cells are connected to each other via elastic connective tissue forming bundles or rings of muscle that contract and stretch as a result of the combined contraction of the constituent muscle fibers;

"Ciliary Body accommodation" or "CBA" refers to the anatomical and physiological changes initiated by the act of voluntary human accommodation, during CB accommodation, impulses from the brain are transmitted to the nerves supplying the ocular tissues so that at least one eye is directed to align its optical axis towards the object of visual fixation, when at least one eye fixates on an object of visual interest, subconscious cues create an approximate estimate of the distance of the object from the eye and CB accommodation is triggered to the appropriate approximate extent required for the image from the object to be sharply focused on the retina, a process of reiterative biofeedback occurs so that the degree of CB accommodation is matched to the required working distance for sharp focus of the image from the object that is being viewed, other physiological actions are also linked to CB accommodation such as convergence (inwards rotation of eyes to triangulate and focus on a near object) and miosis (constriction of pupils to increase visual depth of field);

"Lenticular accommodation" refers to the alteration in optical power of the youthful or pre-presbyopic human eye in response to CB accommodation, the natural human lens is also known as the crystalline lens. It is enclosed within the lens capsule which in turn is connected to the ciliary body via many zonules (also known as suspensory ligaments) that attach close to the peripheral equator of the lens capsule on its posterior and anterior surfaces and extend in a radial fashion, suspending the crystalline lens from the CB. CB accommodation results in increased relative curvature of the front and rear lens capsule surfaces (also known collectively as the capsular bag), and a forward shift in the optical center of the crystalline lens, lenticular accommodation occurs as a result of decreased radial tension in the zonules because CB accommodation causes a relative anterior shift of the ring formed by the center of radial suspension the zonules, the cross sectional diameter of the eyeball is less at the relatively anterior location of the CB ring during CB accommodation, therefore the tension in the zonules is decreased allowing the elastic crystalline lens to revert to a shape that is more rounded in its anterior and posterior curvatures;

"Ciliary Sulcus" Refers to the ring like space bounded posteriorly by the ciliary process and suspensory ligaments of the lens (zonules) and bounded anteriorly by the posterior surface of the iris, the ciliary sulcus is bounded peripherally by the soft tissues overlying the ciliary body, these soft tissues separate the ciliary sulcus from the muscular components of the ciliary body, specifically the circular or annular portions of the ciliary muscle, the meridional portions of the ciliary muscle lie more peripherally and are anchored at the scleral spur, the ciliary sulcus extends for 360 degrees at the base of the iris, is vertically oval in humans and decreases in diameter during CBA:

"UBM" or "Ultrasound biomicroscopy" refers to imaging studies of the eye which show characteristic biometric changes that occur during ciliary body contraction, for understanding of the intended working of embodiments of this present disclosure, it is necessary to define some biometric features that change during CBA:

SSD (sulcus-to-sulcus diameter)—distance between opposite points in the ciliary sulcus, this will vary between individuals due to normal anatomic differences depending on the axial location of the opposite points because the ciliary sulcus is oval instead of circular in the near accommodated state in comparison to the relaxed state as CBA reduces SSD.

ICPA (Iris-ciliary process angle)—the angle between the plane of the iris and the direction of the ciliary process from between which the lens zonules extend to the equator of the capsular bag, ACA (anterior chamber angle)—the angle between the plane of the peripheral iris and the inner layer of the cornea where they meet close to the iris root;

"Annular muscle contraction" or "AMC" refers to the morphological changes occurring during the contraction and relaxation of an annular or sphincteric muscle, specifically, it relates to the shape changes of the round portion of the ciliary muscle during CBA, the ring shaped "round" portion of the ciliary muscle encloses a central opening known as a lumen, which forms the external boundary of the ciliary sulcus, when an annular muscle contracts its total volume remains essentially unchanged but the circle surrounding the lumen in the plane of the lumen constricts, each point lining the lumen moves in relation to its neighbor during contraction and relaxation so that there are no two points that remain stationary relative to each other;

"Elastic biological surface" or "EBS" refers to a flexible membrane that forms the outside enclosure of an annular muscle or other elastic biological surface such as the capsule (or capsular bag) of the crystalline lens;

"Point-to-point contraction linking" or "PPCL" refers to the ability of a device to remain in contact with an elastic biological surface during the entire cycle of contraction and expansion without slipping at its contact points and without offering sufficient resistance to impede movement or cause damage by abrasion or penetration, for a device to be usefully coupled to an annular muscle (such as that found in the CB) it is essential for the device to offer in a predictable manner only as much resistance to movement as is necessary to convert the contraction of the muscle (in this case the contraction associated with CBA) into useful work (in this case IOL accommodation or "IOLA"), effective PPCL depends on critical design elements related to the points of contact of the device to the elastic biological surface, the features in point of contact design to achieve effective PPCL include:

distribution and location—Points of contact should be located around a center of movement that is also the center of movement of the elastic biological surface, number—The points of contact should be numerous enough to maintain stable attachment during motion and distribute resistance evenly across biological surface, at least eight contact points can be desirable for PPCL to a device within the lumen of an annular muscle, too many points of contact if large will limit movement by causing crowding and if small, may impede biological function by causing scarring, size—large contact points in contact with elastic biological surfaces such as the ciliary sulcus or capsular bag will present resistance against contraction or expansion of those surfaces, the continuous expansion and contraction of an annular muscle (even with its surrounding connective tissue) against an inelastic surface is likely to cause damage to biological tissues by abrasion and deposition of eroded tissues, contact points that are too small are likely to cause damage by perforation or penetration into biological tissue, profile—curved contact points offer a variable surface area and some degree of "rocking" during expansion and contraction which protects biological tissue and reduces scarring, multiple protrusions are vulnerable to becoming entangled during implantation, becoming damaged or causing damage to biological tissue;

"Haptic Vaulting" when used in relation to IOLs refers to forward or backward movement of IOL optic in the direction of the visual axis relative to the distal ends of its haptics, in prior art Haptic vaulting is envisioned as a mechanism for achieving IOLA in capsular bag fixated IOLs in response to decreasing diameter of the capsular bag which may vertically compress the haptic ends, Haptic Vaulting may occur surreptitiously in even prior art conventional or monofocal IOLs, depending on nature and placement of the haptics within a fibrosed or contracted capsular bag;

"Rigid Vaulting" when used in relation to IOLs refers to forward or backward movement of IOL optic in the direction of the visual axis relative to the optical nodal point of the eye in response to mechanical forces within the eye, specifically, this relates to movement of an IOL fixed within a capsular bag (IOL-capsule diaphragm) in response to movements of the entire capsular bag caused by:

contraction or relaxation of the zonules attached to the capsular bag secondary to ciliary muscle contraction, variations in fluid pressure (from aqueous humor or vitreous humor) between the anterior and posterior surfaces of the IOL-capsule diaphragm, gravitational shifting of IOL in response to changes in eye position (Rigid Vaulting is widely believed to occur surreptitiously in prior art conventional or monofocal IOLs, but to a variable and unpredictable extent and therefore cannot be relied on to provide useful degree of IOLA);

"Pseudo-accommodation" refers to the retention of some functional unaided near vision in combination with good distance vision following cataract extraction in patients who do not have IOLA, in patients who have a fixed focal length IOL implanted, whose power is set for clear distant vision, it is the ability of such patients to have better than expected (although still limited) near vision (without reading glasses), its existence is due to the following factors or fortuitous conditions:

Pinhole effect—increased depth of field caused by decreasing aperture of the pupil during CBA and in conditions of high illumination, this effect may be enhanced in some lenses whose central curvature is higher than peripheral so that when the peripheral cornea is curtained off by the constricting pupil, the overall focus of the lens because closer, relying on the pinhole effect has the disadvantage of reducing amount of light available to the eye and hence compromising the overall quality of vision, Aspheric optic property of the IOL (Lens has more than one major focal point). This may be intentional or serendipitous: Multifocal IOL design including pupil independent (diffractive lenses, aspheric curvatures) and pupil assisted (linked to pupillary constriction like the pinhole effect but accentuated by the IOL deliberately having a higher power in its central curvature, and Fortuitous/serendipitous optical effects presenting a secondary near image due to lens tilt (induced lenticular astigmatism) and corneal myopic astigmatism (Asymmetry of corneal curvature or tilting of the IOL can cause astigmatism, for example in which vertical lines far away, are seen better than horizontal lines, with the reverse holding try for near, since writing tends be composed of vertical and horizontal lines, people with just the right degree of astigmatism learn to decode the otherwise blurred near vision), and Limited accommodation due to IOL forward movement during CBA which may occur with any IOL implanted in elastic capsular bag with intact zonular attachments where the IOL-capsular bag complex moves forward during CBA increasing the effective power of the IOL and causing its focal point to move from distance to near, younger post cataract patients are often seen to have less need for reading glasses than expected when their (non-accommodating) IOLs have been selected for distant focus in both eyes, it is thought that the combination of a vigorous scarring response (causing the posterior capsule to bind firmly around the edge of the lens, and still strong ciliary muscles, allows the IOL to move forward in a way similar to the natural lens, this effect is usually not of sufficient extent to obviate the need for reading glasses;

"Monovision" refers to the illusion of good near and far vision obtained by implanting a monofocal IOL in one eye whose focal point is for distance and another monofocal IOL in the fellow eye whose focal point is for near. Monovision can also achieve a form of pseudo-accommodation so that when both eyes are used together, one provides good monocular distance vision and the other provides acceptable monocular near vision if the brain is able to adapt to this method of correction, this technique is often not well tolerated and causes reduction in stereoscopic vision, the patient is able to use each eye for its working distance (distance or near) although this does not represent true accommodation;

"IOL accommodation" or "IOLA" refers to a change in the optical focal point of an intraocular lens from a sharp distant focus to a sharp near focus (and intermediate distances when the object of visual attention is in between) in an attempt to simulate is lenticular accommodation in response to CB accommodation, IOL accommodation is not equivalent to the IOL multifocality achieved by multifocal IOLs described immediately below;

"Multifocal IOL" or "MFIOL" refers to an IOL designed to have multiple simultaneous focal point, MFIOLs offer a degree of pseudo accommodation by having multiple focal powers or curvatures molded into a single IOL resulting in images of objects at more than one working distance becoming focused simultaneously on the retina, however, the simultaneous presentation of more than one image by the IOL causes degradation and compromise of each of the images as well as troublesome visual symptoms of halos, glare, ghost images collectively known as dysphotopsia, the providential persistence of pupillary miosis associated with CB accommodation can be utilized to preferentially select the central portion of the IOL curvature for near focusing and allow input from the peripheral lens curvature when CB accommodation is relaxed, and the pupil becomes relatively dilated, however, this type of "pinhole effect" also compromises overall quality of the images and multifocal IOLs in general have limited utility because CB accommodation does not result in true IOL accommodation, the increased range of focus depth of field presented by a static multifocal IOL is offset by lower image quality and visual aberrations, the eye and brain have to learn to ignore the images that are not useful for the current working distance and therefore there is compromise in overall vision quality and comfort;

"Haptic" refers to an arrangement of structural elements whose primary purpose is to hold, support, maintain and fixate one or more other distinct elements or device within the eye, where the device serves a biologically important function;

"Haptic Passenger" refers to a functionally important device supported by the haptic, examples of Haptic Passengers and their associated functions include an optical lens system, a reservoir, depot or container for a therapeutic substance or drug, a diagnostic instrument or sensor, "IOL haptic" or refers to a structural element of an IOL designed to hold an IOL in place within the eye, such as a haptic whose haptic passenger is a lens;

"IOL optic" refers to the optically active component of the IOL having light transmitting refractive power, such as the haptic passenger for an IOL haptic;

"Capsular bag" or "bag" refers to the partially elastic biological membrane which normally contains the lentil shaped crystalline lens of the eye between a front surface (anterior capsule) and a back surface (posterior capsule) which join at the equator of the capsular bag from which equator the lens is suspended from and connected to the processes of the ciliary body by zonules (or suspensory ligaments of the lens), the capsular bag is opened during cataract surgery to remove the cataractous lens by making a roughly circular opening in its anterior capsule, the capsular bag has traditionally been the desired location in which to place an IOL after cataract extraction, the IOL is normally placed through the anterior capsular opening or "rhexis" so that its spring like supporting haptics rest in or close to the equator of the bag, suspending the optic of the IOL within and perpendicular to the visual axis;

"Capsulorhexis" or "rhexis" refers to the surgical opening made in the capsular bag and is a vital step in modern cataract surgery, it is necessary to access the cataract for removal and to insert an IOL if it is to be placed in the capsular bag;

"Posterior capsular fibrosis" or "Posterior capsular opacification" (PCO) refers to the migration and proliferation of fibroblast inside and around the remnants of the capsular bag following cataract surgery, in addition to reducing vision, the scar tissue formed by these fibroblasts causes scarring and contracture of the capsular bag resulting in loss of its elastic properties, posterior capsular fibrosis occurs to at least some extent in the majority of patients following cataract despite various precautions commonly taken to reduce it, contracture of the capsular bag can cause tilt or displacement of an IOL in contact with the bag and will limit post-operative capsular bag movement in response to CBA, the severity of posterior capsular fibrosis is unpredictable but often warrants YAG laser capsulotomy after surgery to break open the capsule when it interferes with vision, the behavior of the capsular remnants following YAG laser capsulotomy is even more unpredictable, this means that any AIOL that relies on capsular bag contraction for functioning is unlikely to be successful because CBA cannot be reliably translated into IOLA by the post-surgical capsular bag;

"Accommodating IOL" or "AIOL" refers to a prosthetic lens or IOL that seeks to restore the function of lenticular accommodation (other than by pseudo-accommodation or monovision) in a patient whose crystalline lens has been removed;

"Simple lens" refers to the concave and convex cross sections depicted in optical drawings and ray diagrams shown commonly in physics textbooks, wherein the convex or concave surfaces enclose a medium whose refractive index is different to that of the media in front and behind the lens, although its front and rear surfaces are separated such a lens has a point (which can actually lie outside the body of the lens) known as the optical center of the lens whose location and optical properties can be described in an idealized fashion by "Thin Lens Theory", and in a more complex, and potentially more accurate fashion by "Thick Lens Theory", the power of such a lens is normally fixed and does not change because the lens is solid and static, the power of a particular simple lens can be made different to that of another by altering one or both of the front and rear curvatures or the refractive index of the medium behind and/or in front of the lens;

"Compound lens" refers to a lens composed of two or more simple lenses whose overall optical parameters can be varied by varying the power of each component lens, varying the separation between the optical centers of the component lenses, and varying other spatial relationship (such as tilt and alignment) between the optical centers or surfaces of the component lenses;

"Flexible lens" refers to a lens composed of an optical medium which is fluid or gel like in mechanical property, and of essentially constant volume, and whose volume is contained and bounded across at least part of its surface by an elastic or flexible membrane, the power of a flexible lens can be varied by shape change of the fluid or gel like medium when such shape changes result in variations in curvature of the flexible membrane when the membrane lies across the visual axis, variation in separation of the front and back surfaces, and variation in location of optical center of lens;

"Biological lens" refers to a lens with front and back surfaces whose body is composed of regions of varying refractive index without clear demarcation or interface between the zones, the regions may be distributed so that the gradient in refractive index varies perpendicular to its optical axis (refractive index changing from center to periphery in a concentric radial fashion) and/or varies in the line of the optical axis so that the refractive index is maximum at the front surface, back surface or center of the lens, variations of the power of a biological lens can be achieved by a spatial redistribution of the regions of high and low refractive indices and may be achieved by overall change in the shape of the lens when it is contained within a flexible membrane or redistribution of the optical centers of the regions of different refractive index without overall shape change of the external boundaries of the lens capsule, resulting in a shifting of the optical center of the lens;

"Neo-biological lens" refers to a lens composed of material whose refractive index can be varied be electronic or photo-chemical means either across the entire material of the lens, or selectively in certain regions; and "Higher Order Aberrations" or "HOA" relates to imperfections of focusing of a nature more complex than lower order optical aberrations such as spherical error and astigmatism, clinically important examples of HOA include spherical aberration, coma and trefoil, correction of HOA can improve visual quality and satisfaction following ocular surgery.

The exact nature and relative importance of various physiological mechanisms active in the human eye during the act of accommodation is controversial. The theory of Helmholtz appears to be the most favored. It is agreed that contractions of the ciliary body/muscle occur in response to neural signals from the brain when accommodation is voluntarily or reflexly initiated. It is also agreed that in the youthful eye, this contraction causes several mechanical changes that result in the optical dioptric power of the lens system becoming more positive and so shifting the focal point of the lens closer to the person. The optical power change is thought to result from an anterior shift of the overall optical center of the lens closer to the cornea and an increase in curvature of the anterior and/or posterior refracting surfaces of the lens (necessitated by the requirement to maintain constant volume within the enclosing capsular bag) when the lentil shaped lens decreases in circumference at its attachment points (zonular fibers) in the plane roughly perpendicular to the visual axis.

In practice, other subtle changes may also contribute to a lesser extent such as constriction of the pupil to induce a pin-hole effect to increase depth of field—pseudo accommodation, shift of the constricted pupillary center away from the relaxed pupillary center to preferentially select a new optical line of site within the eye of different refractive power, and change in lens shape may cause shifting of relative position within the lens, of areas of differing pliability, elasticity and refractive index to cause a change in overall power.

For AIOL design a clear understanding of the anatomical changes occurring in the eye during CBA is desirable. In some species, CBA results in muscular activity that alters the curvature of the cornea or the length of the eyeball amongst other changes, but in humans, alterations of the shape and location of the crystalline lens appear to be the main mediators of accommodation.

When CBA is initiated in humans, at least three muscular sub systems within the ciliary body are activated. First, there is an annular or circular component—a sphincter muscle in the shape of a toroid in a plane approximately perpendicular to the visual axis, located internally to the scleral coat of the eye within the partially elastic parenchyma or connective tissue of the CB. This annular component contracts on accommodation so that the toroid becomes smaller in diameter and thicker in its cross section while the plane of the toroid moves closer to the front of the eye in the line of the visual axis. This contraction releases tension on the lens zonules and capsular bag, thereby causing forward movement of the optical center of the lens and a reduction in the equatorial diameter of the lens capsule.

Second, meridional or longitudinal components that run in approximately parallel to each other slight curve under the sclera connection their relatively stationary attachment on the sclera at one end to the pars plana of the ciliary body at the other end. The effect of contraction of these fibers is to pull the area of attachment of lens zonules anteriorly along the interior surface of the eyeball as it approaches the cornea. The anatomy of the anterior eyeball is such so that this movement results in release in tension of the lens zonules, especially those connecting to the front surface of the lens capsule so that the lens returns to a more rounded shape and its optical center moves forward. The annular fibers of the ciliary muscle lie in a ring separated from the sclera and eyeball by the longitudinal fibers so that the contraction of the longitudinal fibers mechanically facilitates the contraction of the annular components by occupying and increasing the space between the outer aspect of the ring muscles and the sclera.

Third, oblique fibers that run a semi-spiral course under the sclera of the eyeball. They likely act as slings to reduce forces that might inwardly detach the pars plana of the ciliary body and prevent wrinkling of the pars plana of the ciliary body during CBA.

Although the ciliary muscle is usually depicted in cross section, it is actually a complex 3-D structure that is fixed at its outside margin to the sclera of the eyeball and whose inside margin suspends the zonules which connect to the capsular bag. Different species have at least three types of muscle fibers within the ciliary muscle. The exact contribution of the various mechanisms linked to accommodation are not fully known but for the purpose of at least some embodiments of the present disclosure the important points are that when contracted during accommodation the ciliary muscle concentrates into a toroid which decreases in inside diameter, increases in cross sectional area, and moves forward in the plane perpendicular to visual axis with regards to the location of its center of volume.

Contraction of the ciliary muscle leads to changes in the three dimensional shape of the lens capsule as well as displacement of the optical center of the lens in relation to the overall optical center of the eye itself. This displacement alters the overall focal point of the eye allowing variability of focus from distance to near objects.

When accommodation is relaxed in the human eye, outward radial pull via tension in the suspensory ligaments (zonules) of the lens leads to an increase in the circular diameter of the space contained within the lens capsule in the plane approximately perpendicular to the visual axis and path of light from distant objects to the central retina of the eye. The act of accommodation causes the ciliary muscle of the eye to contract which releases tension in the suspensory lens ligaments resulting in reduced diameter of the lens in the visual plane and changes in the anterior and posterior surface curvatures of the lens as well as shifting of the optical center of the lens which result in increased convex diopteric power of the lens and consequently of the whole optical system of the eye allowing near objects to be focused on the retina.

The crystalline lens of the eye is normally flexible and is suspended within an elastic capsule. This capsule has to be penetrated to remove the cataractous lens.

The shape of the lens capsule and enclosed lens in its natural state depends on the interaction between the elastic nature of the capsule and also (a) the tension in the supporting zonules whose force and direction is varied by contraction of the ciliary muscle, (b) resistance and pressure from the vitreous humor against the posterior capsule surface, (c) forces on the anterior surface of the lens capsule from aqueous humor and iris, (d) gravity, and (e) resistance to deformity of the contents of the lens capsule, normally the crystalline lens.

One or more embodiments of the present disclosure utilize biometric changes occuring during CBA. The primary biometric changes utilized are reductions in the sulcus-to-sulcus diameter (SSD), the anterior chamber depth (ACD), the iris-ciliary process angle (ICPA), and the iris-zonula distance (IZD, or posterior chamber depth). Indirect or secondary biometric changes occuring during CBA that can be utilized in one or more embodiments of the present disclosure include reductions in the ciliary process-capsular bag distance (CP-CBD) decreases and the ciliary ring diameter (CRD).

Although there is considerable variability in the exact measured mean values for the various anatomical distance and angles compared in the relaxed and near accommodated state, this is not surprising given the normal anatomical variations between studied individuals as well as the variety of instruments and techniques used in different studies. Additionally, the resolution of the current technology is still sub optimal, as are agreements in precise location of landmarks. Because of the above-mentioned factors, comparison of the various studies shows a wide variability of the mean measured values in both the relaxed and near accommodated state, as well as large standard deviations in the mean difference values. This results in low confidence in the statistical significance of the mean differences in many of the studies. However, at least some embodiments of the present disclosure assume that there are some consistent and predictable variations in measured anatomical parameters during near accommodation including (a) a decrease in the SSD (sulcus-to-sulcus diameter) from approximately 11 mm to approximately 10.5 mm, (b) a decrease in the ICPA (Iris-ciliary process angle) from approximately 40 degrees to approximately 22 degrees, (c) a decrease in the ACA (anterior chamber angle) from approximately 32 degrees to approximately 28 degrees, (d) a decrease in the distance from the ciliary sulcus to the apex of the cornea caused by movement of the plane of the ciliary sulcus anteriorly along the visual axis, and (e) an increase in the diameter of the circular portion of the ciliary muscle. One or more embodiments of the present disclosure can use the above anatomical changes to mechanically link CBA to IOLA in a manner superior to the prior art.

The present disclosure, as demonstrated by the exemplary embodiments described below, can provide an accommodating intraocular lens assembly positionable in the ciliary sulcus. In a first embodiment, shown in FIGS. 1-3, an accommodating intraocular lens assembly 10 can include a plurality of stanchions, such as stanchions 12, 112. Each of the plurality of stanchions can extend between a base end and a distal end. The stanchion 12 extends from a base end 14 and a distal end 16. The stanchion 112 extends from a base end 114 and a distal end 116. The plurality of base ends can be disposed in spaced relation to one another about a first arcuate periphery 18 extending in a first plane. The first plane is referenced at 20 in FIG. 2. The distal ends can be disposed about a second arcuate periphery 22 extending in a second plane. The second plane is referenced at 24 in FIG. 2. The first plane 22 can be spaced from the second plane in a posterior direction along a central optic axis 26. The first arcuate periphery 18 can have a greater radius than the second arcuate periphery 22. The first arcuate periphery 18 and the second arcuate periphery 22 can both be centered on the optic axis 26.

The first arcuate periphery 18 can be positioned in the ciliary sulcus. The base ends can be bulbous and/or at least partially spherical. The plurality of stanchions can extend away from the base ends and the first arcuate periphery 18 toward the second arcuate periphery 22. In the exemplary embodiment, the plurality of stanchions can be wider at the distal end than at the base end. Each of the plurality of stanchions can progressively increase between a first width at the base end to a second width at the distal end in a third plane transverse to the central optic axis 26. The third plane is referenced at 30. Each of the plurality of stanchions can maintain a substantially constant second width (or thickness) in a fourth plane containing the central optic axis 26. The fourth plane is the plane of view of FIG. 2. Narrowing the stanchions proximate to the base ends can minimize the contact area between the assembly 10 and the ciliary sulcus. Also, maintaining a relatively thin cross-section in the fourth plane can be desirable as the space defined by the ciliary sulcus (between the iris and the ciliary muscle) can shrink during contraction of the ciliary muscle and the stanchions can be pinched during contraction of the ciliary muscle.

Each of the plurality of stanchions can extend away from the plane 24 in the posterior direction at an acute angle greater than twenty degrees and less than ninety degrees. The exemplary angle is referenced at 28 in FIG. 2. The posterior direction is referenced at 32 in FIG. 2. The anterior direction is referenced at 34 in FIG. 2.

The accommodating intraocular lens assembly 10 can also include arcuate linking members extending along the first arcuate periphery 18, such as linking members 36, 136. The linking members are not required for all embodiments of the present disclosure but can be desirable for modulating the graph of CBA against IOLA. Duane's graph of accommodation with age is a well-established reference. The amplitude of accommodation is the increase in optical power that an eye can achieve in adjusting its focus. The "amplitude" is defined by a range of object distances for which the retinal image can be sharply. The larger the range of object distances, the larger the amplitude. The amplitude of accommodation is measured during an eye-examination. The closest that a normal eye can focus is typically about 10 cm for a child or young adult. Accommodation then decreases gradually with age, effectively finishing just after age fifty.

Duane's Curve shows that a pre-presbyopic individual (around age 40 or less) has a range or amplitude of accommodation of about 6 diopters or more. A diopter (us) is the unit of measurement of the optical power of a lens and is equal to the reciprocal of the focal length measured in meters (1/meters). It is thus a unit of reciprocal length. For example, a 2 diopter lens brings parallel rays of light to focus at ½ meter$^{-1}$.

Figure 23:
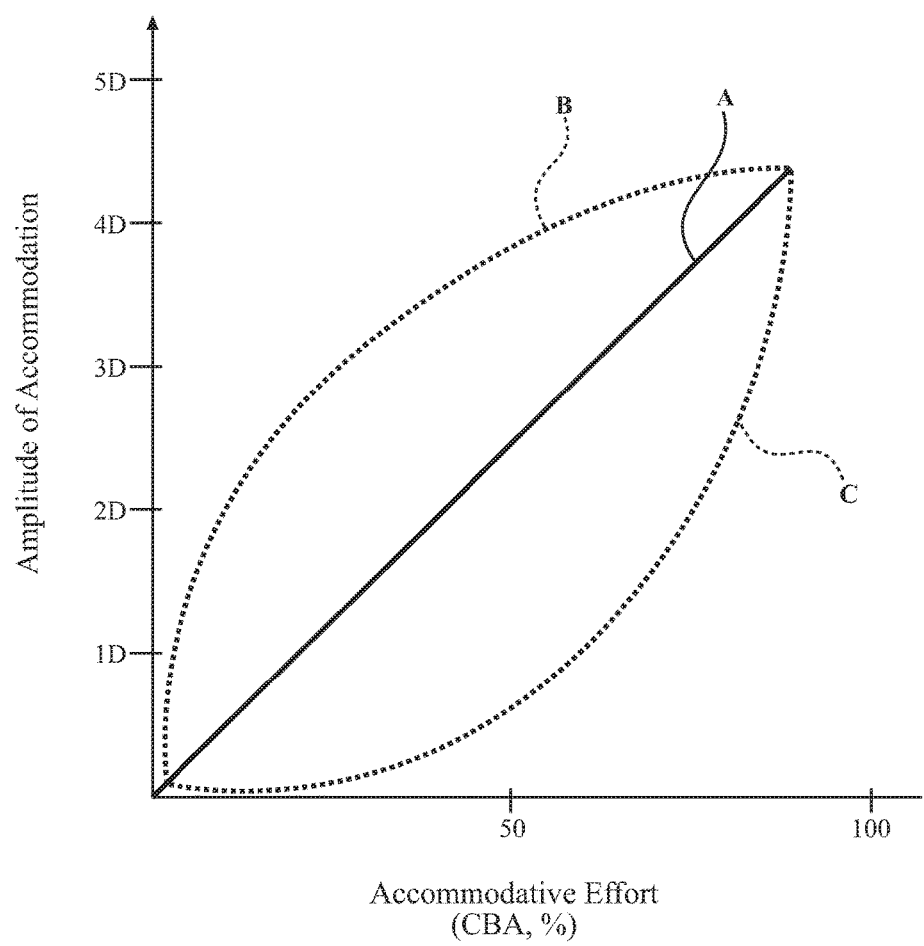
FIG. 23 is a graph correlating an amplitude of accommodation with a percentage of accommodative effort.

An amplitude of 3 to 6 diopters is considered enough to be able to read comfortably if distance vision is perfect. Therefore, a range of 6 D is a useful target for an AIOL. The amplitude of IOLA should have a predictable relationship to accommodative effort (as exerted during CBA by voluntary human effort) as shown in the graph of FIG. 23 as the curve labelled A. The curves labeled B and C are possible curves of AIOLs that can be modified by varying the design of stanchions or by post-operative adjustment (such as with laser energy).

Therefore, an AIOL that merely produces the required degree of accommodation (IOLA) at maximal CBA for near work, has limited utility unless it also provides a smooth transition of accommodative power similar to that achieved by the pre-presbyopic crystalline lens. In fact having a high accommodative power may be a disadvantage if that power is invoked at low levels of CBA or is only available at the extreme accommodative effort because such variations of power may result in disorientating visual fluctuations. The stanchion designs set forth herein (width, flare, curvature, shape, variations in mechanical properties of composite material, etc.) assist in modulating the IOLA to CBA curve. This curve can also be adjusted post-operatively if necessary by application of energy such as laser.

The linking members can also assist with biocompatibility by preventing snagging and also help to minimize deviations from the desired final positions of the stanchions by linking and spacing them apart. The arcuate linking members can interconnect adjacent pairs of base ends. The arcuate linking members do not prevent adjacent base ends from moving relative to each other. The arcuate linking members can be a desirable feature during implantation of the assembly 10, to generally maintain the positions of the base ends. By permitting relative movement of the base ends, the arcuate linking members substantially do not hinder each stanchion from at least some relative movement. The arcuate linking members can be convex relative to the axis 26. When the assembly 10 is implanted, the arcuate linking members can be positioned against the surface of the ciliary muscle. The convex shape allows the arcuate linking members to bias the base ends anteriorly, especially when the ciliary muscle contracts. The linking members can be spaced from both of the base ends 14 and the distal ends 16 along the axis 26. A possible embodiment of such a linking member is shown in phantom in FIG. 1 and referenced at 36'.

The accommodating intraocular lens assembly 10 can also include a positive-power lens 38. The lens 38 can have an anterior side 40 and a posterior side 42 and a center 44 disposed between the anterior side 40 and the posterior side 42. The positive-power lens 38 can be connected with each of the plurality of distal ends whereby the center 44 of the positive power lens 38 is moved along the central optic axis 26 in response to contraction of the first arcuate periphery 18 by contraction of the ciliary muscle.

Figure 8:
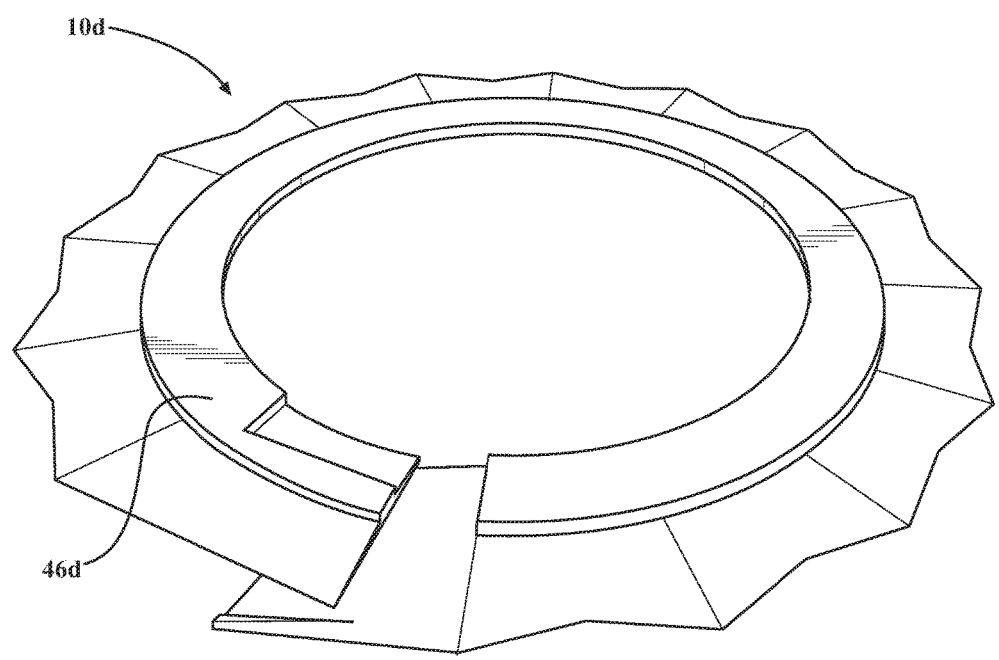
FIG. 8 is a perspective view of an accommodating intraocular lens assembly according to another exemplary embodiment of the present disclosure.

In one or more embodiments of the present disclosure, the lens 38 can be directly connected to the stanchions or can be indirectly connected to the stanchions. In the first exemplary embodiment, the lens 38 can be indirectly connected to the stanchions through a ring member 46. The ring member 46 can be interposed between the positive power lens 38 and each of the plurality of distal ends. The ring member 46 can be a relatively thin, disc structure. The lens 38 can be mounted on the ring member 46 after the ring member 46 and the stanchions have been implanted in the eye. FIG. 8 shows an alternative embodiment of the assembly 10d in which a ring member 46d is discontinuous to ease insertion in the eye. One end of ring member 46d can be moved into an incision in the eye 48 and the remainder of the assembly 10*d* can be drawn into the eye 48.

FIG. 4 is a split cross-sectional view showing the accommodating intraocular lens assembly 10 according to the first exemplary embodiment of the present disclosure position in an eye 48. The eye 48 includes a ciliary muscle 50, an iris 52, a capsular bag 54, zonules 56, and a ciliary sulcus 58. The capsular bag 54 is suspended from the ciliary muscle 50 by the zonules 56. The ciliary sulcus 58 is an annular gap or pocket defined between the iris 52 and an anterior side 60 of the ciliary muscle 50. The shape defined by the ciliary sulcus 58 changes when the ciliary muscle 50 contracts. Generally, a "bottom" of the ciliary sulcus 58 (referenced at 62) shifts toward the axis 26 and also shifts anteriorly when the ciliary muscle 50 changes from a relaxed condition to a contracted condition. The base ends of the assembly 10 can ride along the surface of the ciliary sulcus 58 as the ciliary muscle 50 contracts and relaxes.

The left side of the view of FIG. 4 shows the ciliary muscle 50 in the relaxed condition and the right side of the view shows the ciliary muscle 50 in the contracted condition. In an exemplary operation of the first exemplary embodiment, when the ciliary muscle 50 is relaxed, the lens 38 is disposed at a first position within the eye 48 and the stanchion 12 is disposed at a first angle relative to the lens 38. When the ciliary muscle 50 contracts, the lens 38 is moved to a second position in the eye 48, the second position being anterior to the first position. The lens is referenced at 38' when in the second position. Also, the stanchion 12 is shifted to a second angle relative to the lens 38, the second angle being greater than the first angle. The stanchion is referenced at 12' when disposed at the second angle. The base end 14 is shifted toward the axis 26 and anteriorly when the ciliary muscle 50 contracts. The base end is referenced at 14' when the ciliary muscle 50 is contracted.

Figure 5A:
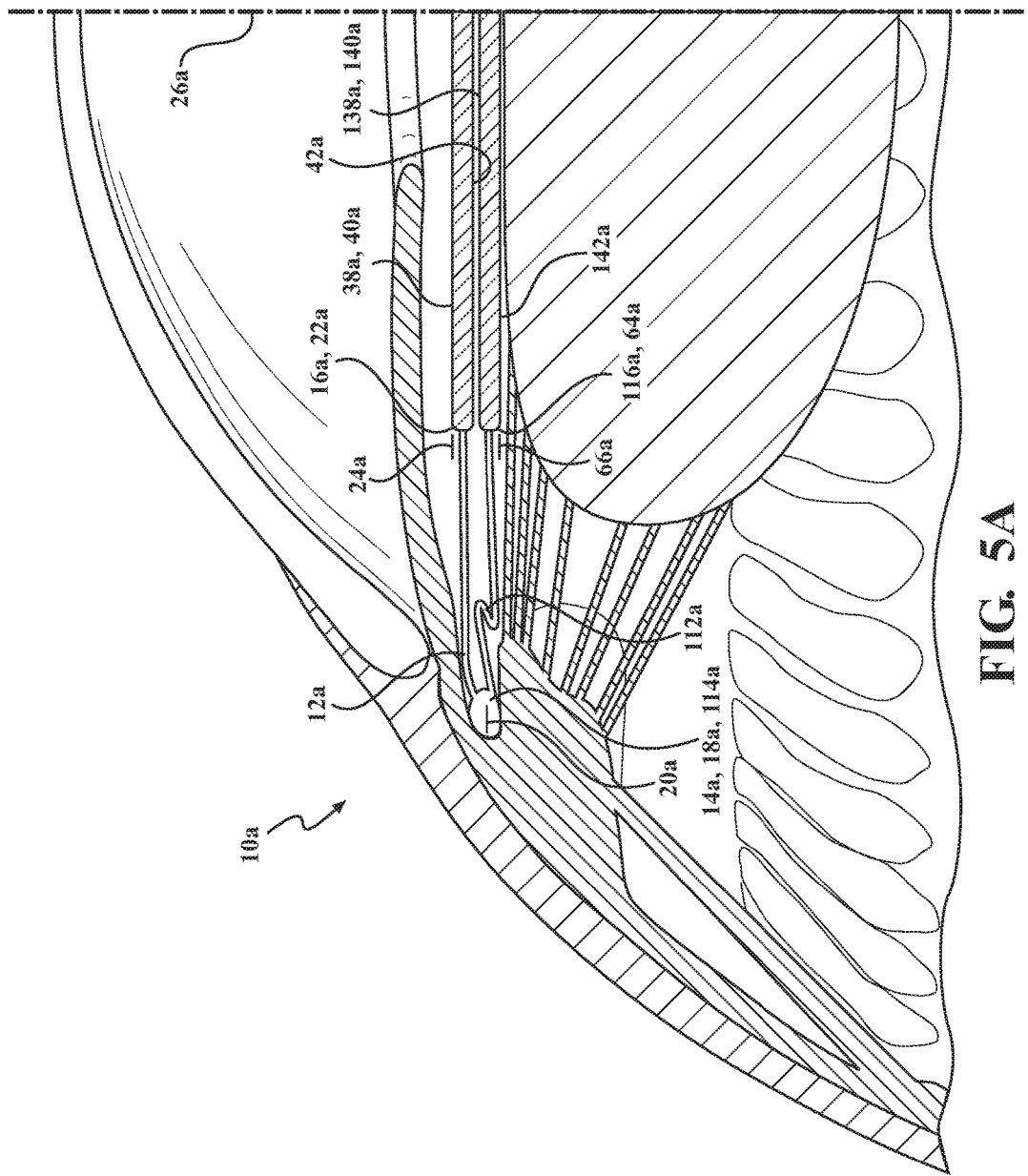
Figure 5B:
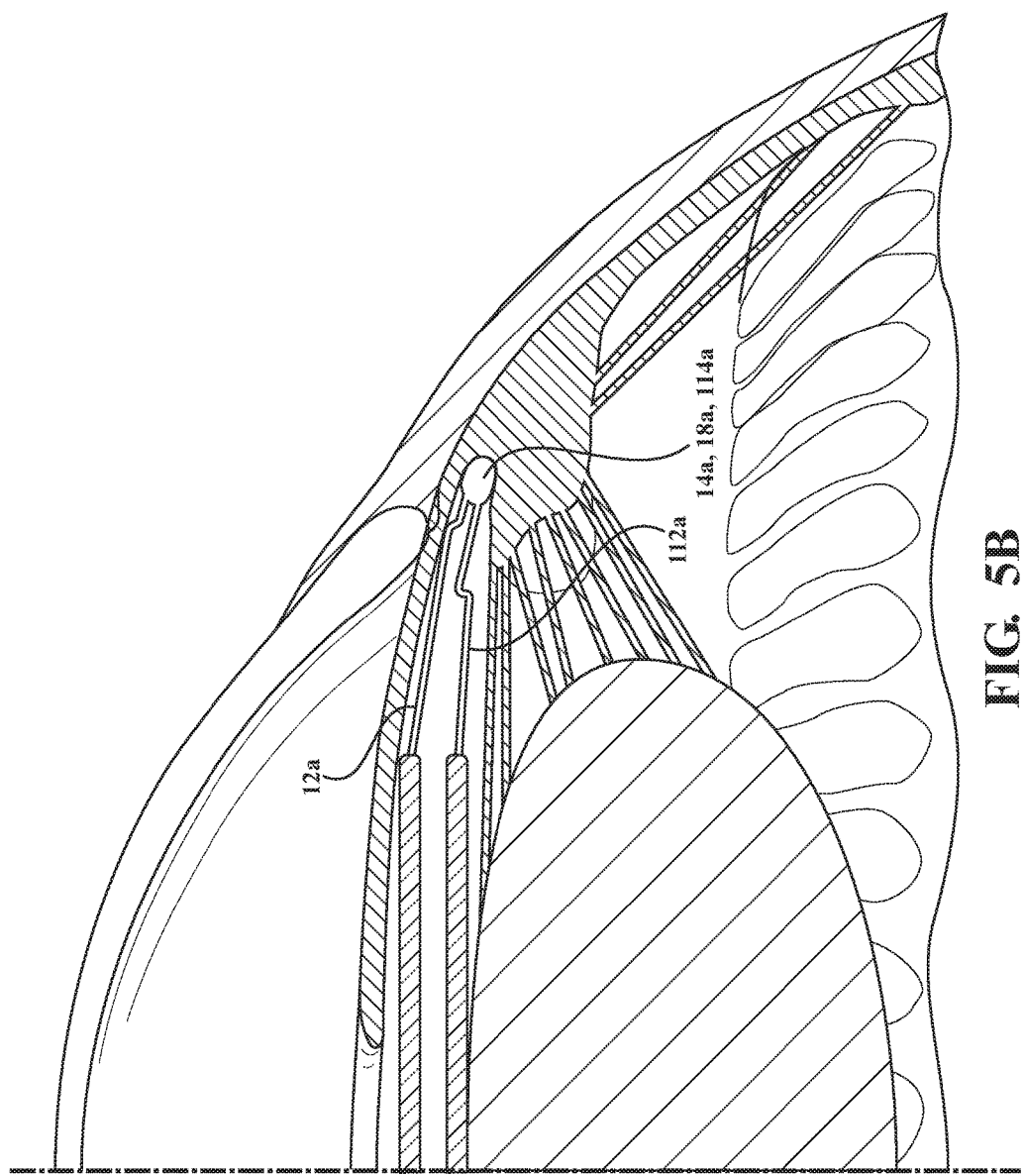

In one or more embodiments of the present disclosure, a plurality of lens can be supported. In a first alternative embodiment, as shown in FIGS. 5A and 5B, an accommodating intraocular lens assembly 10*a* can include a plurality of stanchions each extending between a base end and a distal end, such as stanchion 12*a* with base end 14*a* and distal end 16*a*. The base ends can be disposed in spaced relation to one another about a first arcuate periphery 18*a* extending in a first plane 20*a*. The distal ends can be disposed about a second arcuate periphery 22*a* extending in a second plane 24*a*. The first plane 20*a* can be spaced from the second plane 24*a* in a posterior direction along a central optic axis 26*a*. The first arcuate periphery 18*a* can have a greater radius than the second arcuate periphery 22*a*.

The accommodating intraocular lens assembly 10*a* can also have a positive-power lens 38*a*. The positive-power lens 38*a* can have an anterior 40*a* side and a posterior side 42*a* and a center disposed between the anterior side 40*a* and the posterior side 42*a*. The positive-power lens 38*a* connected with each of the plurality of distal ends whereby the center of the positive power lens 38*a* is moved along the central optic axis 26*a* in response to contraction of the first arcuate periphery 18*a*.

The accommodating intraocular lens assembly 10*a* can also include a second plurality of stanchions each respectively extending between a second base end and a second distal end, such as stanchion 112*a* having base end 114*a* and distal end 116*a*. Each of the base ends of the second plurality of stanchions can be interconnected with one of the base ends of the first plurality of stanchions at intersections and thus be spaced from one another about the first arcuate periphery 18*a*. The second distal ends can be disposed about an arcuate periphery 64*a* extending in a plane 66*a*. The plane 20*a* can be spaced from the plane 66*a* along the central optic axis 26*a* and parallel to the plane 66*a*. The first arcuate periphery 18*a* can have a greater radius than the arcuate periphery 64*a*.

The accommodating intraocular lens assembly 10*a* can also include a secondary lens 138*a* having a second anterior side 140*a* and a second posterior side 142*a* and a second center disposed between the second anterior side 140*a* and the second posterior side 142*a*. The secondary lens 138*a* may or may not be a positive power lens. The second anterior side 140*a* can confront the posterior side 42*a*. The secondary lens 138*a* can be connected with each of the second plurality of distal ends whereby the second center of the secondary lens 138*a* is moved along the central optic axis 26*a* in response to contraction of the third periphery.

In the first alternative embodiment, both of the stanchions 12*a* and 112*a* extend along respective arcuate profiles in a plane containing the central optic axis 26. The views of FIGS. 5A and 5B are in such a plane. The arcuate profile for each stanchion 12*a*, 112*a* is defined by at least one radius and at least one center of curvature. The arcuate profile of the stanchion 112*a* is defined by more than one radius and more than one center of curvature. The arcuate profiles of both stanchions 12*a*, 112*a* extend away from the interconnected base ends 14*a*, 114*a* in the same direction along the central optic axis 26*a*.

FIG. 5A shows the ciliary muscle 50*a* in the relaxed condition and FIG. 5B shows the ciliary muscle 50*a* in the contracted condition. In an exemplary operation of the first alternative embodiment, when the ciliary muscle 50*a* is relaxed, the lens 38*a* is disposed at a first position within the eye 48*a* and the stanchion 12*a* is disposed in a first configuration relative to the lens 38*a*. When the ciliary muscle 50*a* contracts, the lens 38*a* is moved to a second position in the eye 48*a*, the second position being anterior to the first position. The lens is referenced at 38*a*' when in the second position. Also, the stanchion 12*a* is elastically deformed into a second configuration relative to the lens 38*a*. The stanchion is referenced at 12*a*' when disposed in the second configuration. Further, when the ciliary muscle 50*a* is relaxed, the lens 138*a* is disposed at a first position within the eye 48*a* and the stanchion 112*a* is disposed in a first configuration relative to the lens 138*a*. When the ciliary muscle 50*a* contracts, the lens 138*a* is moved to a second position in the eye 48*a*, the second position being posterior to the first position. The secondary lens is referenced at 138*a*' when in the second position. Also, the stanchion 112*a* is elastically deformed into a second configuration relative to the lens 138*a*. The stanchion is referenced at 112*a*' when disposed in the second configuration. A distance between the lenses 38*a* and 138*a* increases when the ciliary muscle 50*a* contracts.

FIG. 5A shows that the stanchion 12*a* includes a first portion extending substantially straight from the positive-power lens 38*a* toward the base end 14*a* in a third plane containing the central optic axis 26*a* and also includes a second portion extending along an arcuate profile in the third plane. The arcuate profile is defined by at least one radius and at least one center of curvature. FIG. 5A also shows the stanchion 112*a* extends along a plurality of arcuate profiles in the plane containing the central optic axis 26*a*. The arcuate profiles are defined by more than one radius and more than one center of curvature in the plane and are separated by a straight section of the stanchion 112*a*. FIG. 5A also shows an acute angle is defined between the stanchion 12*a* and the stanchion 112*a* extending away from one of the intersection of the base end and the second base end. FIG. 5A also shows that the stanchion 12a and the stanchion 112a extend away from the base end 14a and second base end 114a in the same direction along the central optic axis 26a. FIG. 5A also shows the center of curvature of the curved portion of stanchion 12a is posterior of the base end 14a along the central optic axis 26a. FIG. 5A also shows the at least one center of curvature is between the base end 14a and the distal end 16a relative to a direction perpendicular to the central optic axis 26a. FIG. 5A also shows the at least one center of curvature is closer to the base end 14a than the distal end 16a along the direction. FIG. 5A also shows that the accommodating intraocular lens assembly 10a is configured such that the at least one center of curvature is within zonules 56 of the eye 48 when the accommodating intraocular lens assembly 10a is positioned in the eye 48 and the ciliary muscle 50 is relaxed. FIG. 5A also shows that the accommodating intraocular lens assembly 10a is further configured such that the at least one center of curvature is outside of a capsular bag 54 of the eye 48 when the accommodating intraocular lens assembly 10a is positioned in the eye 48 and the ciliary muscle 50 is relaxed. FIG. 5A also shows that the second base end 114a is interconnected to the base end 14a at respective intersections positioned along the first arcuate periphery 18a such that the first arcuate periphery 18a and the third arcuate periphery are coplanar and wherein a thickness of the intersection of the base end 14a and the second base end 114a is greater than a combination of a thickness of the stanchion 12a extending from the intersection and a thickness of the stanchion 112a extending from the intersection. FIG. 5A also shows the stanchion 112a extends along a plurality of arcuate profiles in the plane containing the central optic axis 26a, the arcuate profiles defined by more than one radius or more than one center of curvature in the plane, and wherein a first of the centers of curvature is positioned on an anterior side of the stanchion 112a and a second of the centers of curvature is positioned on a posterior side of the stanchion 112a.

Figure 6A:
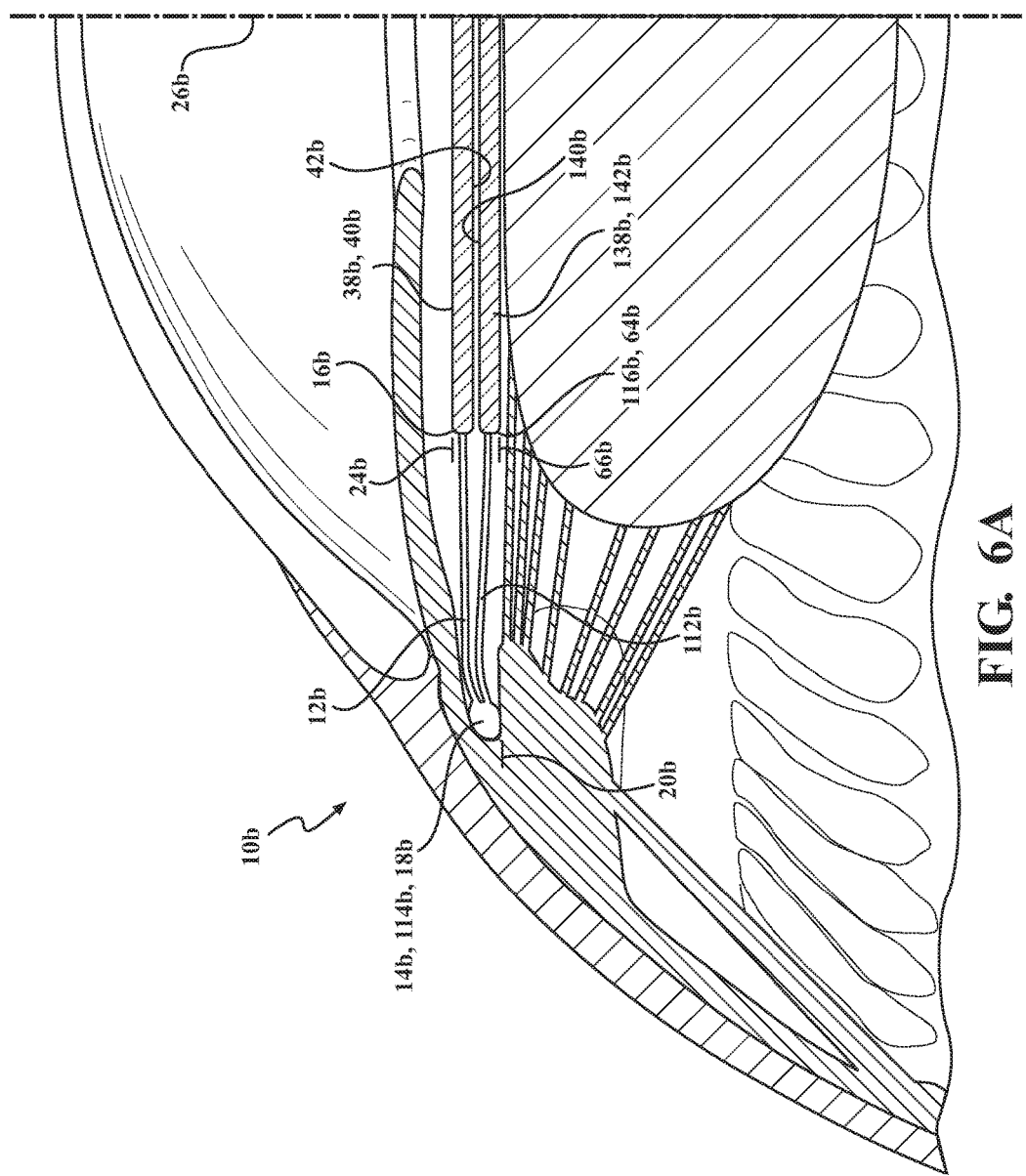
Figure 6B:
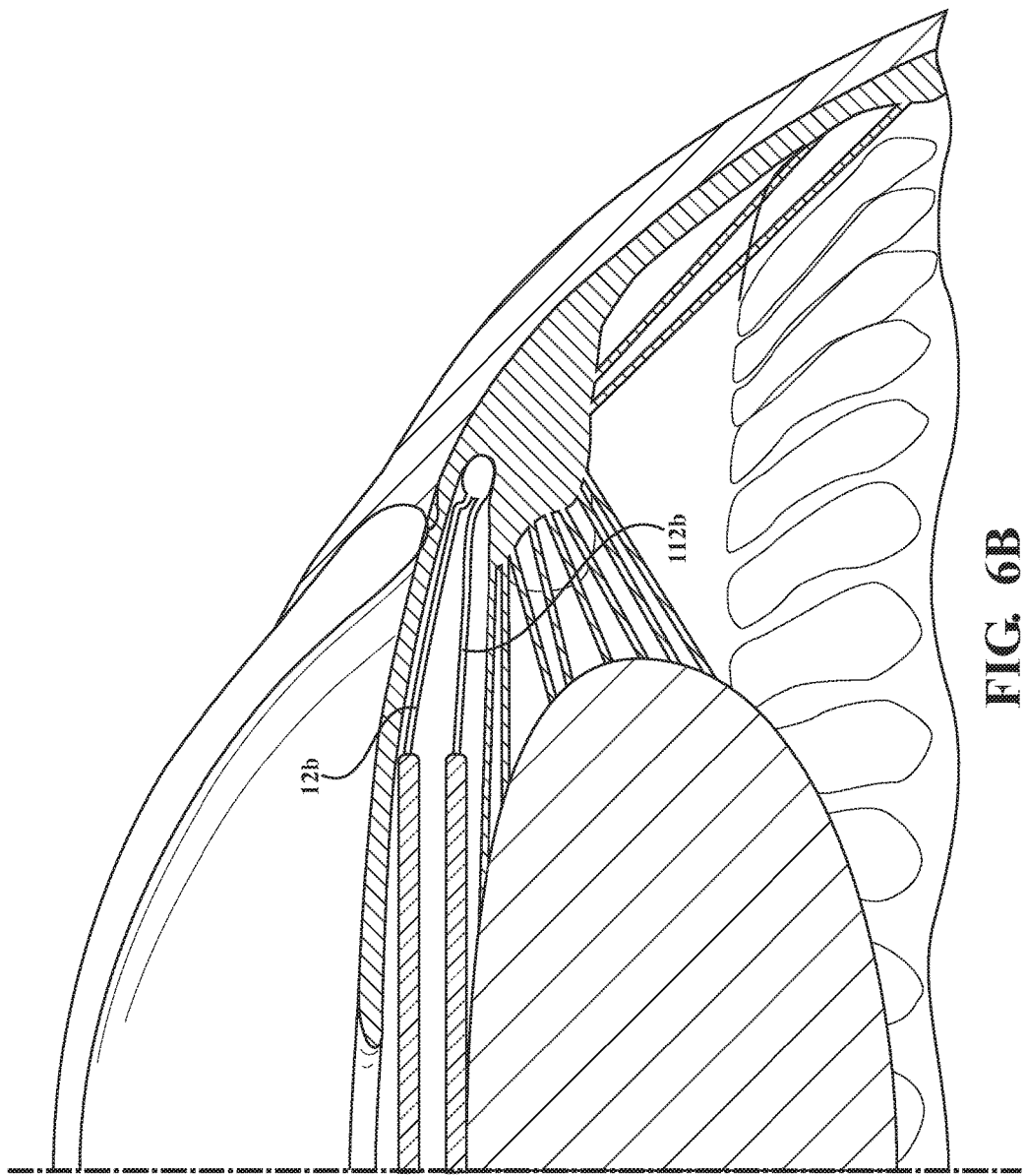

In a second alternative embodiment, as shown in FIGS. 6A and 6B, an accommodating intraocular lens assembly 10b can include a plurality of stanchions each extending between a base end and a distal end, such as stanchion 12b with base end 14b and distal end 16b. The base ends can be disposed in spaced relation to one another about a first arcuate periphery 18b extending in a first plane 20b. The distal ends can be disposed about a second arcuate periphery 22b extending in a second plane 24b. The first plane 20b can be spaced from the second plane 24b in a posterior direction along a central optic axis 26b. The first arcuate periphery 18b can have a greater radius than the second arcuate periphery 22b.

The accommodating intraocular lens assembly 10b can also have a positive-power lens 38b. The positive-power lens 38b can have an anterior 40b side and a posterior side 42b and a center disposed between the anterior side 40b and the posterior side 42b. The positive-power lens 38b connected with each of the plurality of distal ends whereby the center of the positive power lens 38b is moved along the central optic axis 26b in response to contraction of the first arcuate periphery 18b.

The accommodating intraocular lens assembly 10b can also include a second plurality of stanchions each respectively extending between a second base end and a second distal end, such as stanchion 112b having base end 114b and distal end 116b. Each of the base ends of the second plurality of stanchions can be interconnected with one of the base ends of the first plurality of stanchions at intersections and thus be spaced from one another about the first arcuate periphery 18b. The second distal ends can be disposed about an arcuate periphery 64b extending in a plane 66b. The plane 20b can be spaced from the plane 66b along the central optic axis 26b and parallel to the plane 66b. The first arcuate periphery 18b can have a greater radius than the arcuate periphery 64b.

The accommodating intraocular lens assembly 10b can also include a secondary lens 138b having a second anterior side 140b and a second posterior side 142b and a second center disposed between the second anterior side 140b and the second posterior side 142b. The secondary lens 138b may or may not be a positive power lens. The second anterior side 140b can confront the posterior side 42b. The secondary lens 138b can be connected with each of the second plurality of distal ends whereby the second center of the secondary lens 138b is moved along the central optic axis 26b in response to contraction of the third periphery.

In the second alternative embodiment, both of the stanchions 12b and 112b extend along respective arcuate profiles in a plane containing the central optic axis 26. The views of FIGS. 6A and 6B are taken is such a plane. The exemplary arcuate profiles for each stanchion 12b, 112b are defined by one radius and one center of curvature. The arcuate profiles of both stanchions 12b, 112b extend away from the interconnected base ends 14b, 114b in the same direction along the central optic axis 26b.

FIG. 6A shows the ciliary muscle 50b in the relaxed condition and FIG. 6B shows the ciliary muscle 50b in the contracted condition. In an exemplary operation of the first alternative embodiment, when the ciliary muscle 50b is relaxed, the lens 38b is disposed at a first position within the eye 48b and the stanchion 12b is disposed in a first configuration relative to the lens 38b. When the ciliary muscle 50b contracts, the lens 38b is moved to a second position in the eye 48b, the second position being anterior to the first position. The lens is referenced at 38b' when in the second position. Also, the stanchion 12b is elastically deformed into a second configuration relative to the lens 38b. The stanchion is referenced at 12b' when disposed in the second configuration. Further, when the ciliary muscle 50b is relaxed, the lens 138b is disposed at a first position within the eye 48b and the stanchion 112b is disposed in a first configuration relative to the lens 138b. When the ciliary muscle 50b contracts, the lens 138b is moved to a second position in the eye 48b, the second position being anterior to the first position. The secondary lens is referenced at 138b' when in the second position. Also, the stanchion 112b is elastically deformed into a second configuration relative to the lens 138b. The stanchion is referenced at 112b' when disposed in the second configuration. A distance between the lenses 38b and 138b increases when the ciliary muscle 50b contracts.

Figure 7A:
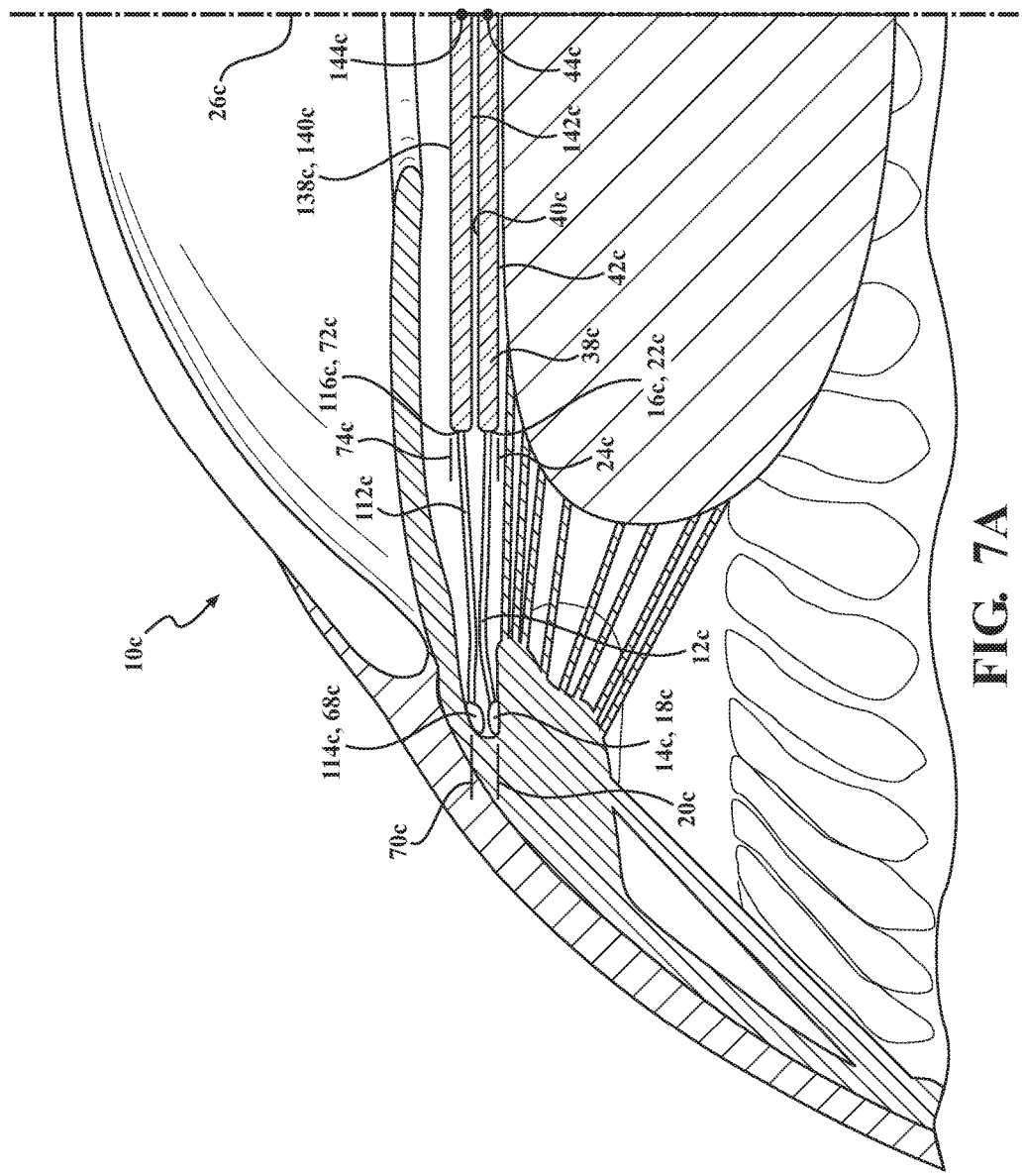

In a third alternative embodiment, as shown in FIGS. 7A and 7B, an accommodating intraocular lens assembly 10c can include a plurality of stanchions each extending between a base end and a distal end, such as stanchion 12c with base end 14c and distal end 16c. The base ends can be disposed in spaced relation to one another about a first arcuate periphery 18c extending in a first plane 20c. The distal ends can be disposed about a second arcuate periphery 22c extending in a second plane 24c. The first plane 20c can be spaced from the second plane 24c in an anterior direction along a central optic axis 26c. The first arcuate periphery 18c can have a greater radius than the second arcuate periphery 22c.

The accommodating intraocular lens assembly 10c can also have a positive-power lens 38c. The positive-power lens 38c can have an anterior 40c side and a posterior side 42c and a center 44c disposed between the anterior side 40c and the posterior side 42c. The positive-power lens 38c connected with each of the plurality of distal ends whereby the center 44c of the positive power lens 38c is moved along the central optic axis 26c in response to contraction of the first arcuate periphery 18c.

The accommodating intraocular lens assembly 10c can also include a second plurality of stanchions each respectively extending between a second base end and a second distal end, such as stanchion 112c having base end 114c and distal end 116c. The base ends 114c can be spaced from one another about an arcuate periphery 68c extending in a plane 70c. The second distal ends can be disposed about an arcuate periphery 72c extending in a plane 74c. The planes 70c and 74c can be spaced from one another and from the planes 20c and 24c along the central optic axis 26c. The arcuate periphery 68c can have a greater radius than the arcuate periphery 72c.

The accommodating intraocular lens assembly 10c can also include a secondary lens 138c having a second anterior side 140c and a second posterior side 142c and a second center 144c disposed between the second anterior side 140c and the second posterior side 142c. The secondary lens 138c may or may not be a positive power lens. The second posterior side 142c can confront the anterior side 40c. The secondary lens 138c can be connected with each of the second plurality of distal ends whereby the second center 144c of the secondary lens 138c is moved along the central optic axis 26c in response to contraction of the third periphery.

In the second alternative embodiment, both of the stanchions 12c and 112c extend along respective arcuate profiles in a plane containing the central optic axis 26c. The views of FIGS. 7A and 7B are taken in such a plane. The exemplary arcuate profiles for each stanchion 12c, 112c are defined by a plurality of radii and centers of curvature. The arcuate profiles of both stanchions 12c, 112c extend away from the respective base ends 14c, 114c toward one another along the central optic axis 26c.

FIG. 7A shows the ciliary muscle 50c in the relaxed condition and FIG. 7B shows the ciliary muscle 50c in the contracted condition. In an exemplary operation of the first alternative embodiment, when the ciliary muscle 50c is relaxed, the lens 38c is disposed at a first position within the eye 48c and the stanchion 12c is disposed in a first configuration relative to the lens 38c. When the ciliary muscle 50c contracts, the lens 38c is moved to a second position in the eye 48c, the second position being posterior to the first position. The lens is referenced at 38c' when in the second position. Also, the stanchion 12c is elastically deformed into a second configuration relative to the lens 38c. The stanchion is referenced at 12c' when disposed in the second configuration. Further, when the ciliary muscle 50c is relaxed, the lens 138c is disposed at a first position within the eye 48c and the stanchion 112c is disposed in a first configuration relative to the lens 138c. When the ciliary muscle 50c contracts, the lens 138c is moved to a second position in the eye 48c, the second position being anterior to the first position. The secondary lens is referenced at 138c' when in the second position. Also, the stanchion 112c is elastically deformed into a second configuration relative to the lens 138c. The stanchion is referenced at 112c' when disposed in the second configuration. A distance between the lenses 38c and 138c increases when the ciliary muscle 50c contracts.

Although the cross sections of FIGS. 7A and 7B show non-connected stanchions that may respond better to pinching in the ciliary sulcus, it can be desirable that some of the intervening stanchion pairs should be connected to each other to increase the likelihood that the anterior and posterior ring members/lens remain in apposition relative to each other. Otherwise, the anterior and posterior ring members/lens may not stay together during implantation.

Figure 9A:
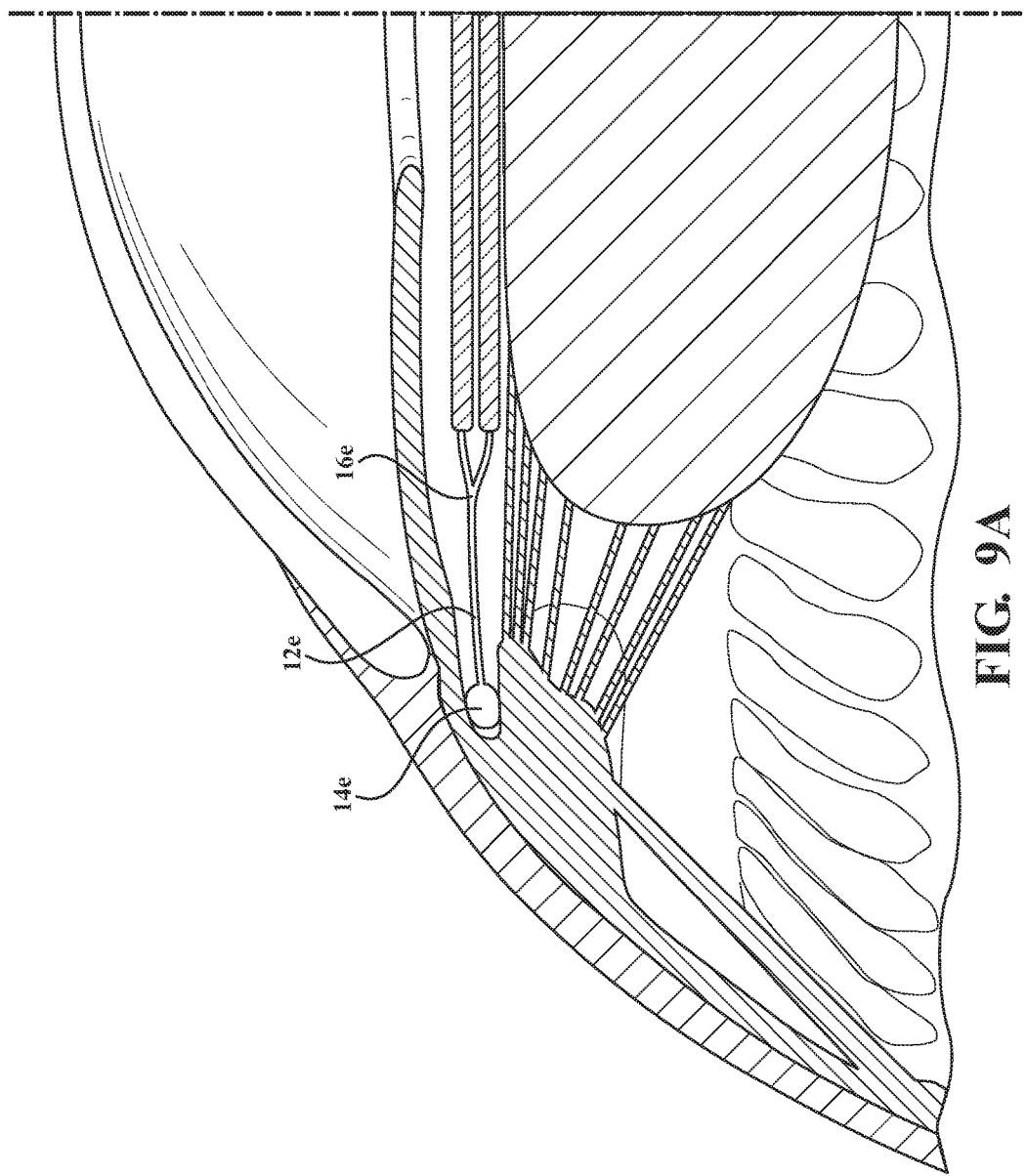
Figure 9B:
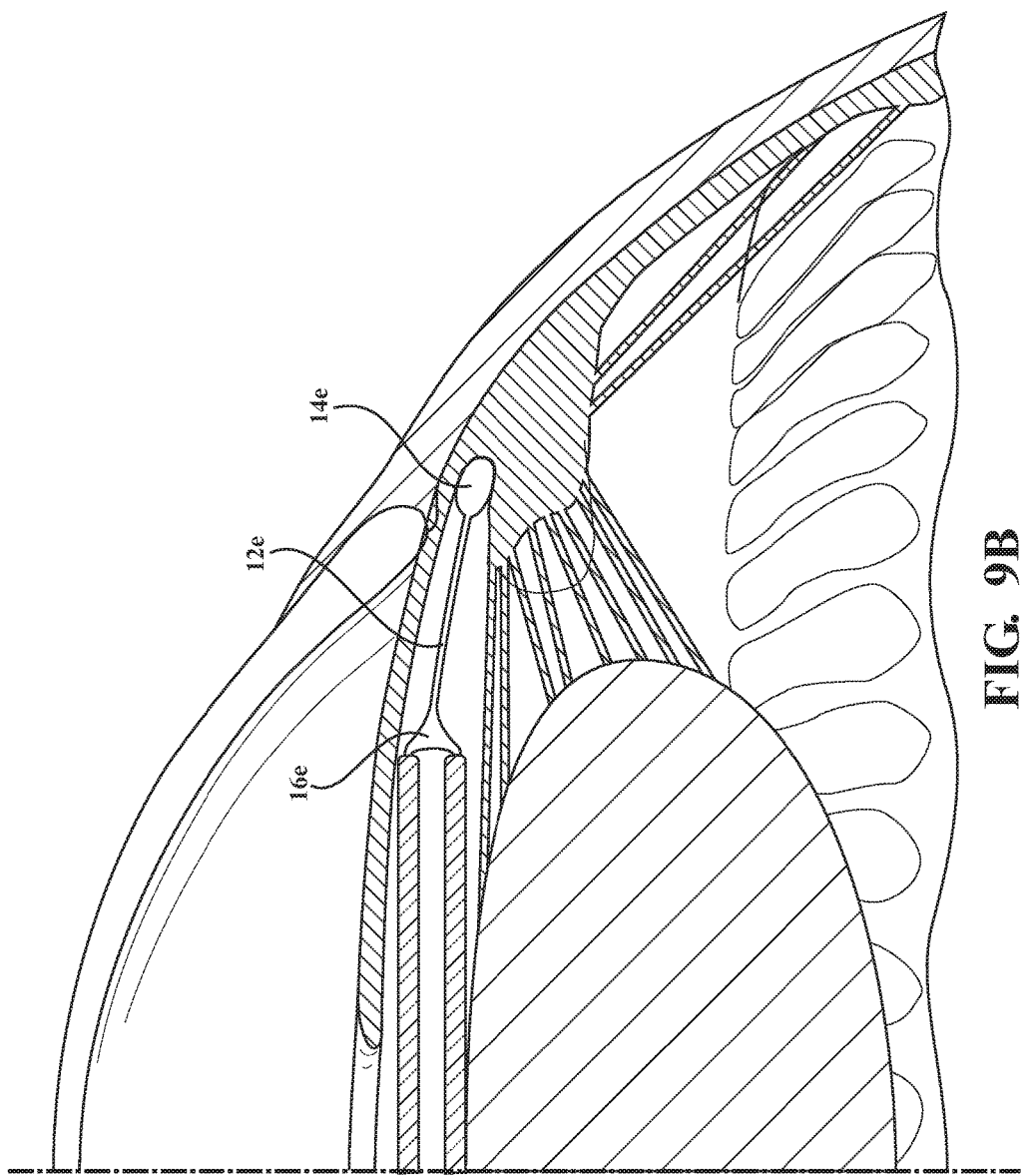

In one or more embodiments of the present disclosure, at least one of the plurality of stanchions can contain fluid. The stanchion can be filled with fluid prior to implantation in the eye or after being implanted. For example, as shown in FIGS. 9A and 9B, a stanchion 12e can extend between a base end 14e and a distal end 16e. The stanchion 12e can be elastically deformable so that the bulbous base end 14e is compressed during contraction of the ciliary sulcus and thereby expand a bellows-like distal end 16e. The distal end 16e can elastically expand when the ciliary muscle contracts. First and second lenses 38e and 138e can be engaged with the distal end 16e and spaced locations on the distal end 16e. When the stanchion 12e is compressed, fluid is directable out of the base end 14e to expand the distal end 16e. Elastic deformation of the distal end 16e can cause the lenses 38e, 138e to change position relative to one another. FIG. 9A shows the arrangement when the ciliary sulcus is relaxed and FIG. 9B shows the arrangement when the ciliary sulcus is contracted. The lenses 38e, 138e are further apart from one another in FIG. 9B.

Figure 10:
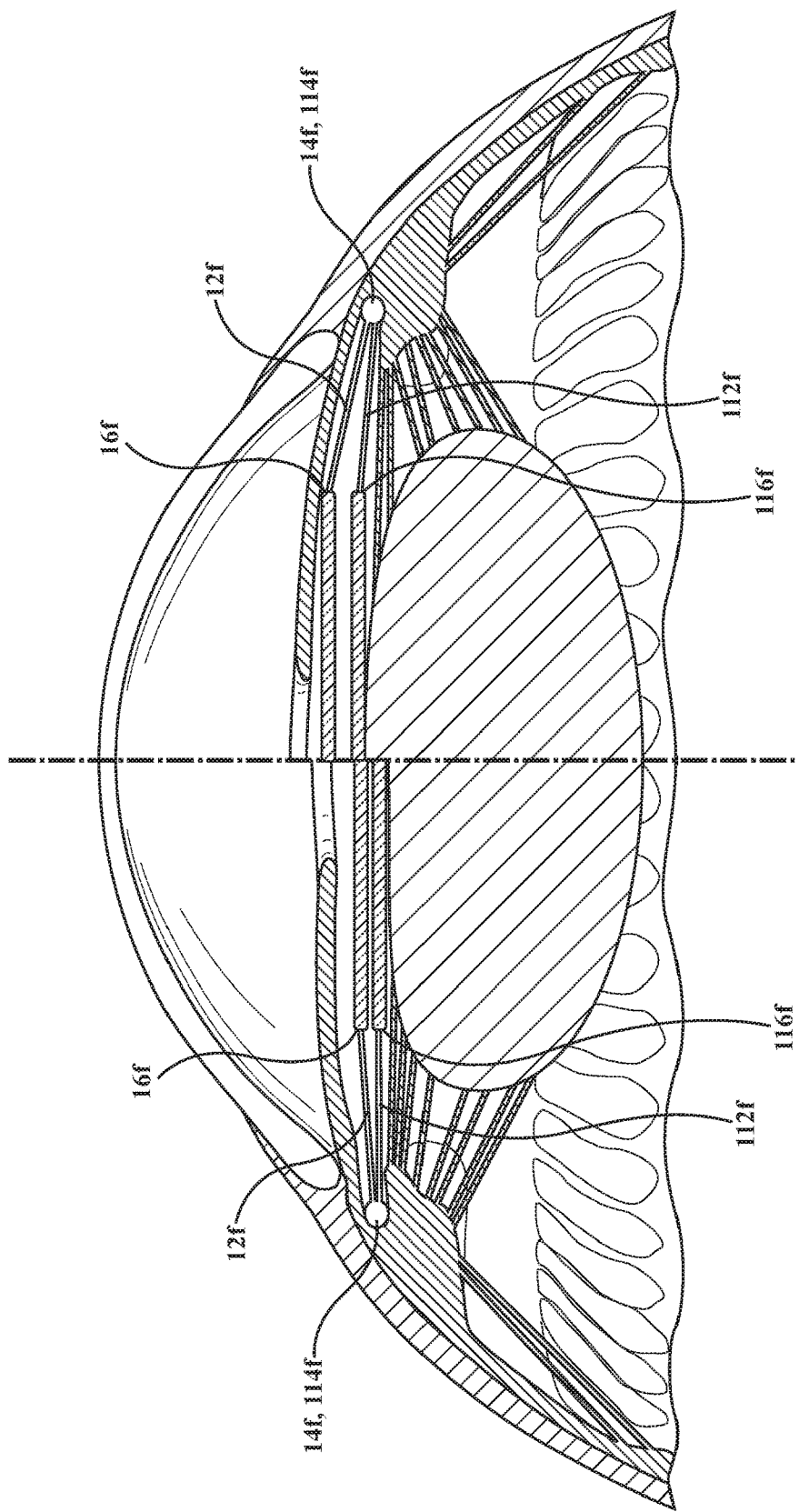
FIG. 10 is a split cross-sectional view showing the accommodating intraocular lens assembly according to another exemplary embodiment of the present disclosure position in an eye, wherein the left side of the view shows the ciliary muscle in the relaxed condition and the right side of the view shows the ciliary muscle in the contracted condition.

FIG. 10 shows a third alternative embodiment wherein a first plurality of stanchions 12f extends along a first substantially straight profile in a plane containing the central optic axis 26f and a second plurality of stanchions 112f extends along a second substantially straight profile in the plane containing the central optic axis 26f. The first substantially straight profile and the second substantially straight profile extend away from the respective base end 14f and second base end 114f in the opposite directions along the central optic axis 26f. The stanchions 12f extend anteriorly and the stanchions 112f extend posteriorly.

Figure 11:
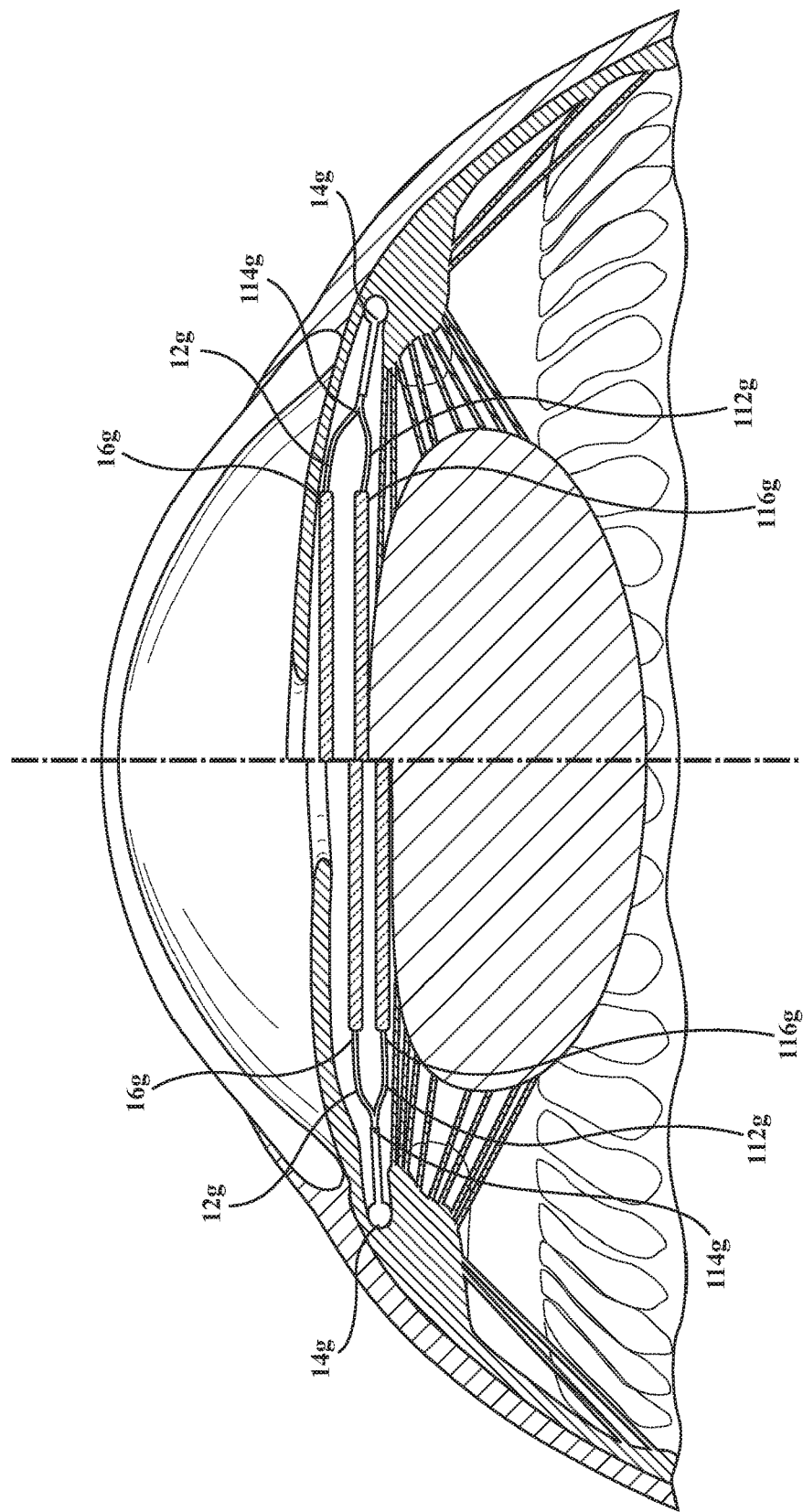
FIG. 11 is a split cross-sectional view showing the accommodating intraocular lens assembly according to another exemplary embodiment of the present disclosure position in an eye, wherein the left side of the view shows the ciliary muscle in the relaxed condition and the right side of the view shows the ciliary muscle in the contracted condition.

FIG. 11 shows a fourth alternative embodiment wherein each of a first plurality of stanchions 12g extends between a base end 14g and a distal end 16g. Each of a second plurality of stanchions 112g extends between a base end 114g and a distal end 116g. Each of the second base ends 114g is mounted on one of said plurality of stanchions 12g.

Figure 12:
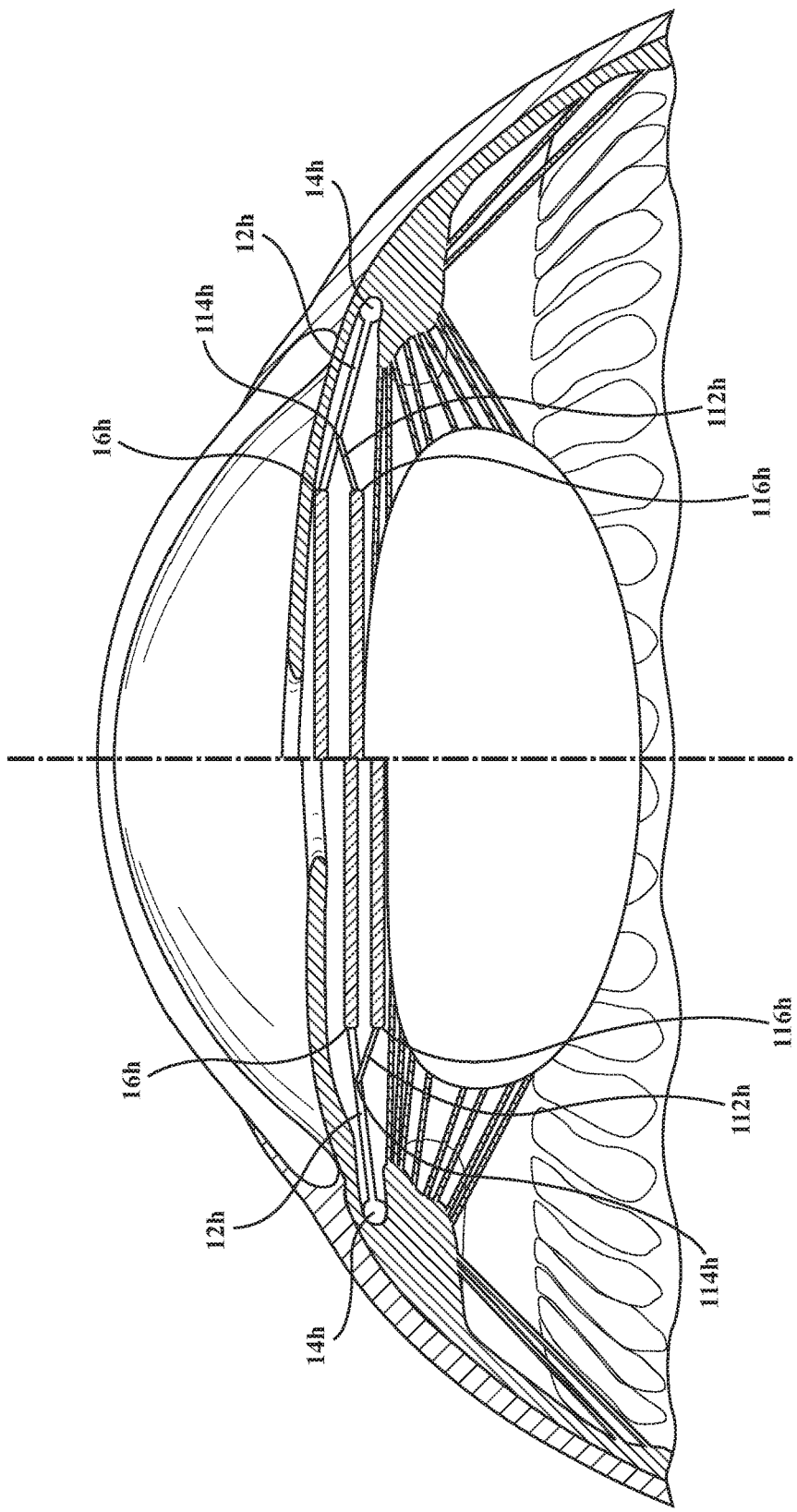
FIG. 12 is a split cross-sectional view showing the accommodating intraocular lens assembly according to another exemplary embodiment of the present disclosure position in an eye, wherein the left side of the view shows the ciliary muscle in the relaxed condition and the right side of the view shows the ciliary muscle in the contracted condition.

FIG. 12 shows another alternative embodiment wherein each of a first plurality of stanchions 12h extends between a base end 14h and a distal end 16h. Each of a second plurality of stanchions 112h extends between a base end 114h and a distal end 116h. Each of the second base ends 114h is mounted on one of said plurality of stanchions 12h. It is noted that in FIG. 12 the capsular bag is illustrated as empty and devoid of a crystalline lens to confirm that an AIOL according to one or more embodiments of the present disclosure is an alternative to the natural lens and that the function of an AIOL according to one or more embodiments of the present disclosure can occur independent of any capsular bag changes.

Figure 13:
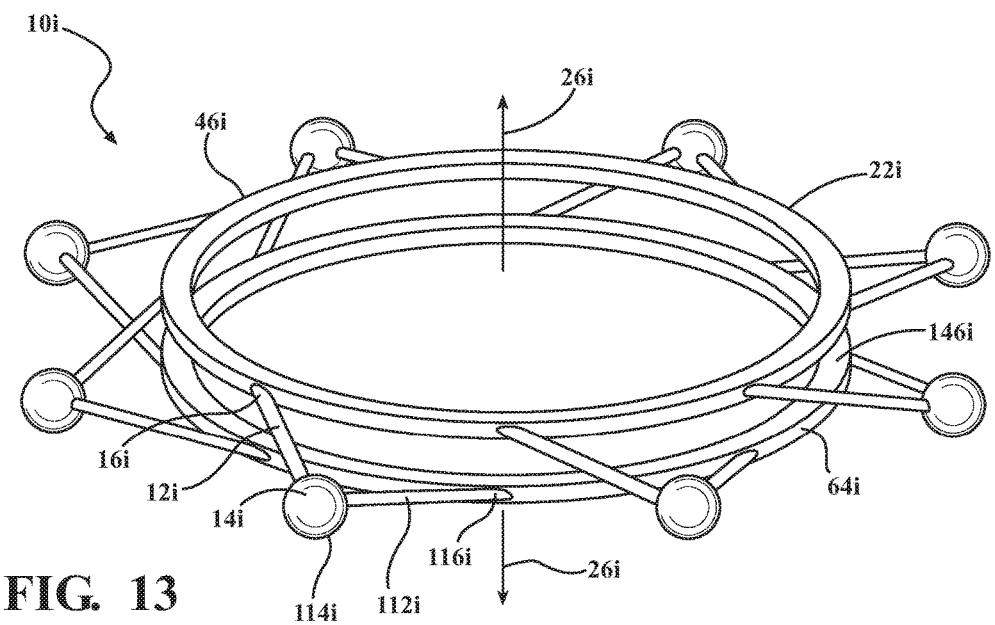
FIG. 13 is a perspective view of an accommodating intraocular lens assembly according to another exemplary embodiment of the present disclosure.
Figure 15:
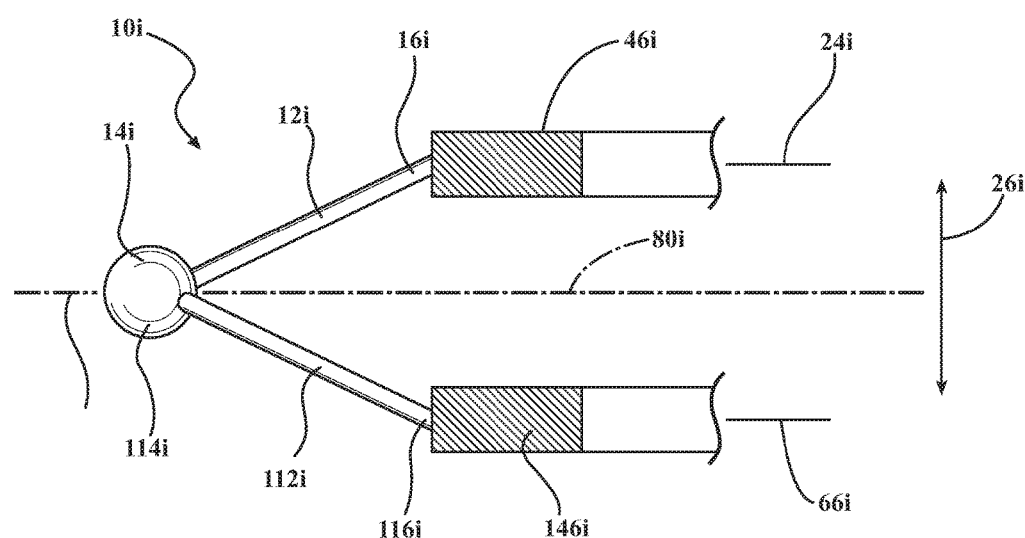
FIG. 15 is a side view of the exemplary embodiment shown in FIG. 13.
Figure 14:
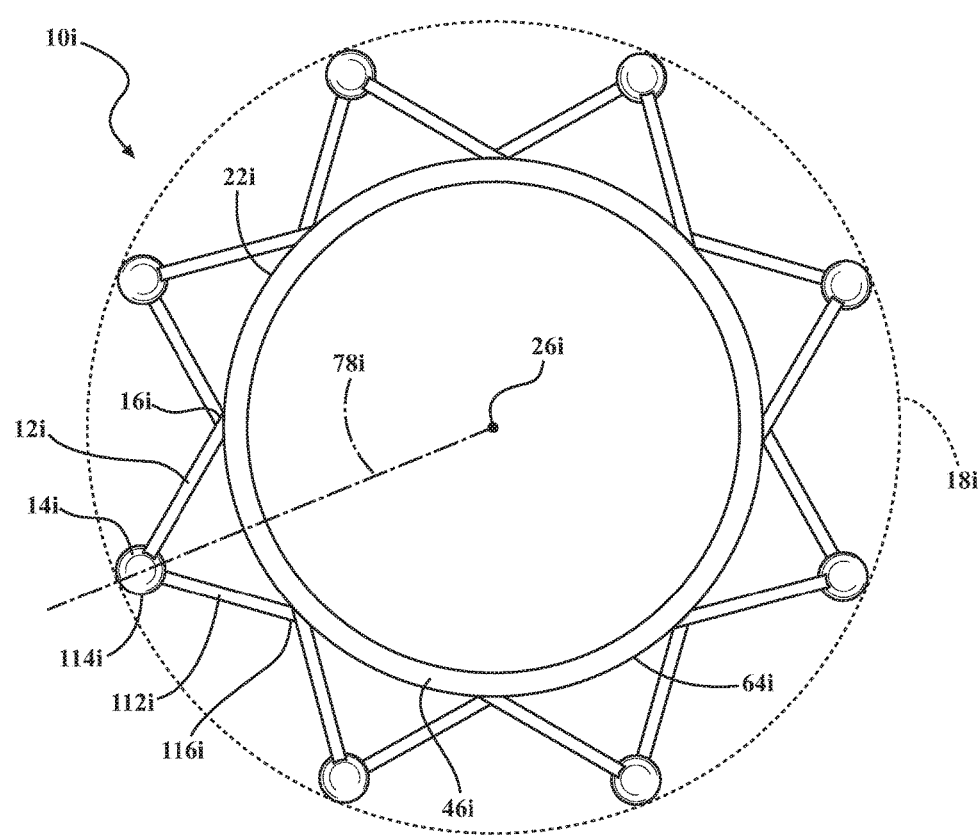
FIG. 14 is a top view of the exemplary embodiment shown in FIG. 13.

In another alternative embodiment, as shown in FIGS. 13-15, an accommodating intraocular lens assembly 10i can include a plurality of stanchions each extending between a base end and a distal end, such as stanchion 12i with base end 14i and distal end 16i. The base ends can be disposed in spaced relation to one another about a first arcuate periphery

18i extending in a first plane 20i. The distal ends can be disposed about a second arcuate periphery 22i extending in a second plane 24i. The first plane 20i can be spaced from the second plane 24i in a posterior direction along a central optic axis 26i. The first arcuate periphery 18i can have a greater radius than the second arcuate periphery 22i.

The accommodating intraocular lens assembly 10i can also include a ring member 46i. The ring member 46i can be interconnected with each of the plurality of distal ends 16i. The ring member 46i can be a relatively thin, disc structure. A haptic passenger such as a lens can be mounted on the ring member 46i after the ring member 46i and the stanchions 12i have been implanted in the eye.

The accommodating intraocular lens assembly 10i can also include a second plurality of stanchions each respectively extending between a second base end and a second distal end, such as stanchion 112i having base end 114i and distal end 116i. Each of the base ends of the second plurality of stanchions can be interconnected with one of the base ends of the first plurality of stanchions at intersections and thus be spaced from one another about the first arcuate periphery 18i. The second distal ends can be disposed about an arcuate periphery 64i extending in a plane 66i. The plane 20i can be spaced from the plane 66i along the central optic axis 26i and parallel to the plane 66i. The first arcuate periphery 18i can have a greater radius than the arcuate periphery 64i.

The accommodating intraocular lens assembly 10i can also include a ring member 146i. The ring member 146i can be interconnected with each of the plurality of distal ends 116i. The ring member 146i can be a relatively thin, disc structure. A haptic passenger such as a lens can be mounted on the ring member 146i after the ring member 146i and the stanchions 112i have been implanted in the eye.

The stanchions 12i each extend along a first path transverse to and spaced from the central optic axis 26i in a first plane transverse the central optic axis 26i. FIG. 14 is a view of such a plane. Each of the second plurality of stanchions 112i extends along a second path that is transverse to and spaced from the central optic axis 26i in the first plane. The first path and the second path are mirrored with respect one another in the first plane about a first axis 78i extending between the base end 14i, 114i and the central optic axis 26i in the first plane. This is shown in FIG. 14. The first path and the second path are mirrored with respect one another in a second plane containing the central optic axis 26i about a second axis 80i extending between the base end 14i, 114i and the central optic axis 26i in the second plane. This second plane is shown in FIG. 15.

The embodiment of the present disclosure illustrated in FIGS. 13-15 can be viewed as a coiled, double ring embodiment. The embodiment can be configured and sized for placement in the anterior chamber, the ciliary sulcus, or the capsular bag. The embodiment can be configured to support and hold (1) a biometric intraocular sensor to measure and transmit/display data such as intra-ocular pressure, (2) a drug delivery system to release medication within eye, (3) a mechanical supporting device particularly useful for the treatment of glaucoma by opening drainage channels for aqueous humor within the eye and/or for supporting and stabilizing ocular structures such as the iris or lens capsule to facilitate intraocular surgery, and/or (4) supporting an intraocular lens especially AIOL located either in the sulcus or the capsular bag being dual or single optic and modular or one-piece.

Embodiments of the present disclosure, including a ring member, stanchions, and the haptic passenger, should be made from biocompatible materials that fulfil necessary requirement so strength, flexibility and elastic memory, such requirements varying depending on the ring member morphology. Morphology options can include ring members empty in the center. The ring members may be empty centrally for purposes of modular attachment of haptic passengers so that their circumferences can be made oblate to allow insertion through an incision considerably smaller than their largest diameter in the relaxed state. Uniformly flexible ring members empty in the center can be squeezed into an oval shape or twisted into a figure-of-eight shape. Ring members can have varying flexibility, empty in the center with or without hinges arranged around their periphery. These ring members fold at specified junctions to deform into a heart shape or a double loop. Morphology options can also include ring members that are a solid disc shape. In such case they may be folded into a spiral cylindrical roll, a roughly semicircular (taco) shape along its diameter, concertina fashion through an injector, or a combination of these options to allow insertion through an incision considerably smaller than their largest diameter in the relaxed state.

An array of flexible stanchions can connect the two partly deformable ring members so that the structure can exist in three states. In a vivo state or relaxed state, pairs of stanchions are attached by their distal ends near the periphery of opposite ring members with each stanchion radiating away from the center of the ring and making contact with the base end of its paired stanchion. The paired stanchions are arranged so that they meet in a third plane between the planes of the two ring members. The junctions of the base ends of the stanchion pairs describe an approximate circle (maximum haptic circle) whose diameter is greater than either of the two ring members. The length, angle and flexibility of the stanchions is configured so that the maximum haptic circle matches the perimeter of the ocular anatomy to which the haptic carrier is to attach: anterior chamber angle, ciliary sulcus or capsular bag.

In a coiled state or packed state, the planes of the ring members are closely positioned to each other along the visual axis. In this state, the flexible stanchions are coiled and sequestered between the two ring members whose edges can be shaped so that they approximate a protected circular enclosure when the ring members are drawn closer by rotation. The purpose of the enclosure is to protect the coiled stanchions so that they will not cause damage to or be damaged by ocular structures during insertion and placement. The coiled state is achieved by the ring members being rotated relative to one another in an axis passing through their centers. The rotation has the effect of drawing in and straightening out the base stanchion junctions so that the diameter of the Maximum haptic circle is decreased. The ring member having a smaller diameter can serve as a bobbin around which the stanchions are wound.

The elastic and mechanical properties of the stanchion materials can be of a certain nature so that they coil and uncoil without slipping out of alignment, and a cylindrical frame may need to be placed within the stanchions to guide their coiling in the same manner that drums are used to wind cable. For optimal function a third ring may be used intermediate in size between the ring member having a larger diameter and the ring member having a smaller diameter, placed adjacent to the ring member having a smaller diameter. The third ring can serve as a frame with apertures through which the stanchions pass. Its function is to facilitate coiling or winding of the stanchions by laying and guiding them into proper position in an enclosed space between the third ring and the ring member having a smaller diameter.

In the coiled state, spontaneous uncoiling is prevented by one or both of two mechanisms can be prevented by the planes of the two ring members being in close alignment so that the uncoiling forces are contained by the rigidity of the ring member having a larger diameter until equilibrium is disrupted by the mechanical separation between the planes of the ring members, such as with the use of using a lever instrument of the type commonly used in ocular surgery. Uncoiling can also be prevented by a mechanical stopper such as a pin, knob or wedge that prevents relative movement between the ring members until it is removed.

In the third state, a transition state or insertion state, the coiled ring members can be grasped with an insertion instrument or placed within an injector cartridge so that their dimensions are suitable for passage through a small incision and placement within the eye. This state occurs after the coiled state and before the in vivo state. In this state, the ring members are either flattened if hollow in their center, or folded if not hollow in their center, such temporary deformation being necessary to maximize the ring diameters that may fit within the smallest desirable incision. If a mechanical stopper has been used to maintain the coiled state it is removed once the ring members have been deformed because spontaneous uncoiling is prevented by the deformation and the stopper is no longer necessary. Once the haptic carrier is placed in the desired location it is released and the deformed ring members return slowly to their "coiled state" shape. Once the haptic carrier is close to its coiled state, it will begin to spontaneously uncoil because of the absence of any mechanical stopper or because a lever instrument is then used to separate the ring members. As the planes of the ring members separate, the spontaneous uncoiling of the ring members will cause the stanchions to expand outwards in a plane between the ring member members until the proper anatomical location is reached.

Coiled ring embodiments could feasibly be packaged in the transition state after manufacture and such a "pre-loaded cartridge" has desirable features but has the drawback of placing high demands on the elastic memory of the material requiring relatively precise return to its original shape after having been stored in a stressed state for several months. A compromise solution could be to place and store the IOL inside a sealed cartridge in the unfolded state. The cartridge can be designed so that one side is attached to a syringe or plunger mechanism while the other side has a tapering fluted tube through which the IOL is pushed by the plunger once the tip of the tube has been placed into the incision. The design of the tube folds the IOL so that it fits through the narrow opening and then unfolds once in place.

Coiled-ring embodiments can provide several benefits. The stanchions can be protected by a sleeve during insertion and placement thus preventing crimping and breakage. Ocular structures can be protected by a sleeve so that a smooth profile is presented at sites of friction such as incision, iris and capsule thus preventing damage to these structures. A reduced arc of space is occupied during unfolding, which protects ocular structures. Because the haptic passenger only occupies one plane (in the empty center versions), abrasion against intra-ocular structures is minimized as the IOL unfolds. In prior art, unfolding of the IOL typically occurs in a sweeping arcuate fashion like the movements of wings, which requires a considerable amount of unobstructed volume within the eye if the IOL is not to touch ocular structures other than those it is designed to rest against. It is particularly important to minimize touch or abrasion against the inner lining of the cornea (endothelial layer) and the iris. The coiled ring design with empty center minimizes risk of endothelial cell damage due to uncoiling in one plane rather than arcuate sweep unfolding of prior art. In the case of a solid disc design, even though the IOL will occupy more than one plane when it is folded into a semicircle or taco, the fact that the stanchions will not expand outwards until the IOL has resumed an approximately flat discoid shape means that the volume of excursion within the eye will still be considerable less than in the prior art. Another benefit is that the coiled-ring arrangement can allow for multiple stanchion support (8 or more) rather than conventional two spring haptics or four point plate haptic resulting in better centration and greater stability and reduced risk of dislocation. Further, the coiled-ring arrangement minimizes the volume of material required for the IOL by use of a compact design that allows expansion after insertion, which is ideal for dual optic IOL (accommodating or even non-accommodating) and for modular IOL.

It is noted that one or more embodiments of the present disclosure can be formed from materials that can be modified after the lens assembly is implanted in the eye. For example, at least one mechanical property of at least one of the plurality of stanchions can be modified after the implanting. A mechanical property can at least partially define how the stanchion behaves under loading. In one or more embodiment, the modification can be carried out by applying electromagnetic energy to a portion of the at least one of the plurality of stanchions and thereby modifying an elasticity of the at least one of the plurality of stanchions.

One or more embodiments of the present disclosure can provide a Haptic design that maintains stability of its Haptic Passenger in the ciliary sulcus during ocular movement due to its shape and size. The haptic can be composed of stanchions which attach to the circumference of a fixed ring member at one end, and whose other ends describe a circular oval that forms a variable "virtual ring." The planar separation of the fixed ring member and the virtual ring can be dependent on the angles formed by the stanchions relative to the rings, while their lengths can remain essentially constant.

One or more embodiments of the present disclosure can prevent dislocation by gravity, inertia and flow of intraocular fluids, and mechanical forces exerted by adjacent intraocular structures both static and dynamic. The stability can be achieved by the size, shape, and/or composition of the haptic arrangement with the size being selected on the basis of pre-operative measurements made on each patient. The components that define the virtual ring (delineated by base end of stanchions) can be arranged so that they form a an oval circle of a variable diameter whose maximum extent corresponds to that of the ciliary sulcus (SSD) when CBA is relaxed and whose minimum extent corresponds to the diameter of the ciliary sulcus (SSD) when CBA is maximally activated. The said diameter can be oval shaped rather than strictly circular, to conform to the shape of the human ciliary sulcus.

The virtual ring of contact elements (base end of stanchions) can be made of a size and shape that fit securely into the ends of the ciliary sulcus without slippage or biological damage. The material can be bio-compatible and deformable but have sufficient structural memory to be folded prior to insertion into the eye through a small corneal incision and then unfolded into position within the ciliary sulcus of the eye.

The haptic design can thus be suited by dimensions and material of composition for stable and accurate surgical placement in the ciliary sulcus of the human eye between the anterior face of the lens capsule and zonules, and the posterior surface of the iris. A first anatomical change caused by CBA can be utilized by one or more embodiments of the present disclosure as shape-changing mechanisms is the decrease in diameter of the ciliary sulcus (perpendicular to the visual axis) due to annular contraction. This is measured as a decrease in the sulcus to sulcus diameter (SSD) which causes the virtual ring to contract, increasing separation of between fixed and virtual rings and so moving the fixed ring member and haptic passenger forward towards the cornea relative to the plane of the SSD circle. A second anatomical change can be anterior movement of the ciliary sulcus due to CB contraction. This causes forward movement of the plane of the SSD circle relative to the fixed points of the ocular globe caused by ciliary muscle contraction, resulting in forward movement of the virtual ring towards the cornea, which is additive in effect to the forward movement of the fixed ring member caused by reduction in SSD. A third anatomical change can be anterio-posterior pressure or compression at the ciliary sulcus between the zonules and the posterior surface of the iris due to forward movement of the ciliary body. Anterio-posterior pinching occurring in the ciliary sulcus due to annular contraction of the ciliary muscle results in increased compression at the ciliary sulcus from anatomical "crowding" against the posterior surface of the iris.

Ciliary sulcus placement effectively harnesses the three main functional elements of the ciliary muscle (longitudinal, oblique and annular) which on ciliary muscle contraction generate mechanical force that is matched to movements of single or multiple optic IOLS. Ciliary body contraction forces can be thus used to convert contraction to anterior displacement of the ring member of fixed circumference offset from the plane of the contracting circle. May be single or double (dual optic), convert contraction to move pins or pistons relative to a tangential bar or ring, and squeeze fluid. This allows a single or dual optic design in the configuration whereby equatorial reduction in circumference of an approximately circular anatomical trench associated with the ciliary muscle allows purchase on multiple contact points causing a corresponding reduction in circumference of the circle joining the contact points so that the contact pints contract in relation to each other without the need for sliding relative to the circular anatomical trench. The contact points serving as hinges whose relative movement is translated into variation of optical power to allow for close focusing on objects when accommodation is voluntarily initiated by contraction of the ciliary muscle. The movement described can be either increased separation of multiple optics of the IOL or forward movement of the center of a single optic.

One or more embodiments of the present disclosure can provide a Haptic design that is well suited for safe insertion through a small incision by being composed of multiple spoke like flexible elements arranged in a radial fashion connecting at least one fixed ring member to a virtual ring.

One or more embodiments of the present disclosure can define a star-like structure with individual radii converging at a central nexus to support a Haptic Passenger. Intermediate radii can be joined by a circular band of varying width and thickness running tangentially to the radii serving to shield and space out the elements, provide redundant support for safety, and prevent protrusions or deformations that catch against biological structures during injection and unfolding, presenting a planar profile for insertion into ciliary sulcus. The periphery of the radii can serve as contact points against anchoring structures within the eye.

The anterior-posterior hinged struts (stanchions) incorporated into "cogwheel" shaped sheets joined at edges are amenable to work in the ciliary sulcus. The requirement of predictable flexibility and elastic memory retention in response to small variations in mechanical forces needed when the lens is in situ, conflicts with the requirement for extreme deformability needed to fold and unfold the lens. The designs and shapes described above is best suited to overcome these difficulties.

Other benefits include efficient mechanical linkage with ciliary body contraction whether placed in capsular bag or ciliary sulcus. Multiple, flexible interconnected struts provide error correction for asymmetry and minor mis-positioning as well as some redundancy in case of damage during insertion. Small bulk allows for easy folding for insertion. Further, the performance does not depend on integrity of capsular bag (or zonules when placed in sulcus).

One or more embodiments of the present disclosure can provide a Haptic design that moves in harmony with internal ocular structures. The haptic flexes, contracts, expands and changes shape in a reversible manner in response to, and while in apposition with dynamic intraocular structures such as annular muscles, elastic capsules, supporting fibers and ocular connective tissue without presenting mechanical resistance that may damage ocular structures during such repeated and reversible mechanical changes.

A desirable aspect of one or more embodiments of the present disclosure can be point-to-point contraction linking (PPCL) in which the contact points are multiple enough to distribute force and support, spaced horizontally, vertically and all other important intermediate meridians, and large enough to provide support and make contact without damage but small enough and/or curved to offer minimal resistance to and friction against elastic dynamically contracting intra-ocular structures such as annular muscles or elastic capsules.

One or more embodiments of the present disclosure can provide a Haptic design whose cyclic movements in response to internal ocular structures can be used to predictably alter the force, tension and spatial separation between its constituent elements.

One or more embodiments of the present disclosure can provide a Haptic design composed of elements that are rigid and connected at certain points but flexible and elastically jointed at others so that may move in relation to one another and the eye but maintain stable fixation overall once implanted in the eye.

One or more embodiments of the present disclosure can provide a Haptic design that compresses in response to CB contraction in a predictable manner without significantly impeding CB contraction by virtue of point-to-point deformability. By thus compressing in response to CB contraction, one or more embodiments of the present disclosure can provide a Haptic design that links anatomical changes occurring during CBA, to variations in mechanical forces between the elements of the haptic. By virtue of the variation of force, tension and spacing between the elements of the rigid but elastically jointed haptics applies forces on the Haptic Passenger.

One or more embodiments of the present disclosure can provide a Haptic design in which the cyclic variations of force, tension and separation between its constituent elements can be linked to predictable variations in the properties of the Haptic Passenger. In the specific case where the Haptic Passenger is an optical lens system or "optic," the power of the optic can be reversibly and predictably varied through various mechanisms depending on the design of the lens system.

An approach for predictably and reversibly varying optical power in an IOL that is focused for distance in the non-accommodative state in order to achieve IOLA (beyond pseudo-accommodation) in various biologically feasible IOL systems include a "Simple lens." The power of a simple lens can be reversibly varied by changing its location relative to the optical center of the eye by vaulting or moving forward during CBA. This is achieved in the Jester's collar design (ring member with stanchions having decreasing width away from the ring member) by forward movement of the optic caused by point-to-point contraction.

An approach for predictably and reversibly varying optical power in an IOL that is focused for distance in the non-accommodative state in order to achieve IOLA (beyond pseudo-accommodation) in various biologically feasible IOL systems also includes a "Compound lens." The power of a dual optic IOL can be reversibly varied by changing the separation of the optics. This can be achieved through the double Jester's collar design or in the single Jester's collar design by any other means whereby one optic is fixed closer to the haptics at their contact points and the other optic further away so that CB contraction results in separation of the two optics.

An approach for predictably and reversibly varying optical power in an IOL that is focused for distance in the non-accommodative state in order to achieve IOLA (beyond pseudo-accommodation) in various biologically feasible IOL systems also includes a "Flexible lens." The power of a flexible lens can be reversibly varied by pinching, squeezing or compressing the flexible periphery of the lens to cause increased power by increasing the relative curvatures or relative separation of the anterior and posterior surfaces. In the Jester's Collar design this effect can be achieved by giving the optic element a flexible periphery and mounting it between the flaps of the collar (the stanchions extending away from the ring member) so that points on the flexible periphery are attached to the inner surface of the haptic elements and become compressed during CBA, in turn compressing the periphery and achieving the desired power change.

An approach for predictably and reversibly varying optical power in an IOL that is focused for distance in the non-accommodative state in order to achieve IOLA (beyond pseudo-accommodation) in various biologically feasible IOL systems also includes a "Biological lens." A biological lens as described for the purposes of the present disclosure is that which most closely approximates the natural, youthful crystalline lens of the human eye. Technological constraints have hitherto prevented the manufacture of such a lens for prosthetic use. If such prosthesis could be manufactured and assembled within the eye, it could be fixed in place between the haptic elements in the same fashion as that described for the flexible lens above and could have its power reversible varied in the same fashion by compression of its periphery between the haptics.

An approach for predictably and reversibly varying optical power in an IOL that is focused for distance in the non-accommodative state in order to achieve IOLA (beyond pseudo-accommodation) in various biologically feasible IOL systems also includes a "Neo-biological lens." A neo-biological lens as described for the purposes of the present disclosure would be an IOL whose power can be varied by electronic or photo-chemical means either across the entire material of the lens, or selectively in certain regions. Practical application of this type of lens is limited by the available technology, but should it be manufactured, its power could be controlled in many ways by the haptic linked to CBA as described above.

One or more embodiments of the present disclosure can provide a Haptic design which when manufactured to the appropriate dimensions is well suited for placement within the capsular bag of the eye. One or more embodiments of the present disclosure can provide a Haptic design allowing for attachment of the Haptic Passenger after the Haptic has been implanted in the eye so that the Haptic can be placed within the eye before the insertion of the Haptic Passenger. One or more embodiments of the present disclosure can provide a Haptic design that when placed prior to capsule rhexis provides stability and support of the lens capsule, which facilitates the performance of surgery. One or more embodiments of the present disclosure can provide a Haptic design that when placed prior to capsule rhexis can be adapted to improve pupillary dilation and thus facilitates the performance of surgery.

For desirable placement and harnessing of the ciliary body power, it may be desirable to have a two component IOL system in which the haptic passenger (a single or dual optic IOL) is attached within the eye to a ring-shaped haptic. The haptic itself is circular flat disc open in the center which can be implanted in the ciliary sulcus after an incision is made but before the anterior capsule is opened (capsulorhexis, or simply rhexis). This ring would confer some additional benefits in performance of the surgery such as maintaining AC depth and preventing rapid fluctuations to protect zonules, holding anterior capsule taught to improve capsulorhexis, providing a potential platform for (detachable) iris hooks or iris lip to improve pupillary dilation, providing secure anchor linked to ciliary sulcus to against which optic/haptic complex can be placed to transmit kinetic force of ciliary muscle contraction and convert it to optical changes in IOL power, and providing a ring member for potential post-operative mechanical/optical property modification by selective application of laser energy.

One or more embodiments of the present disclosure can provide a haptic that can be implanted separately from the haptic passenger, which has the advantage that it can be placed within the eye without the optic (or other haptic passenger). If the haptic passenger does not present an obstruction to surgery (such as that presented by a centrally located optic), it may be implanted at an earlier stage of surgery and thus facilitate subsequent steps of the surgical procedure. The modular IOL allows a two stage implantation. A first benefit of the two stage implantation are that it allows the haptic to be securely placed and seated in the ciliary sulcus before further surgical steps distort the anatomy around the ciliary sulcus. A haptic unfolded behind the iris is almost certain to become located in the ciliary sulcus because its posterior migration is limited by the anterior surface of a lens. It cannot pass beyond the anterior capsule, as the anterior capsule of the lens is still intact at this stage of the surgery. A second benefit is that the haptic can incorporated benefits of other surgical devices without the separate need for these devices, such as pupil expanders and anterior chamber stabilizing rings.

Design considerations for haptic in modular (two stage) IOL system include the area of touch wherein the slant of ring member and curve of the stanchions can be optimized by mathematical modeling to enhance refractive change per unit of ciliary muscle contraction, optic configurations such as can use single, dual or multiple optic configurations to simulate accommodation, allowing the ring member to have a gap (open or horseshoe shape) to allow for easier introduction past iris and assist with iris displacement or be a continuous circle, the inside edge can have a groove to accommodate optic, and the optic can have lip to fix against ring member at one end and two other lips or snaps to fix into place.

One or more embodiments of the present disclosure can provide a Haptic design that occupies and stretches the area adjacent to the ciliary body of the eye in a manner that may increase aqueous humor outflow and treat glaucoma following surgery. This is a novel concept and does not rely on a modular, two stage IOL (or any of the other elements of the ring member design other than ciliary sulcus placement) but on the design of the stanchion elements and interconnecting bands/rings so that they cause stretching and tension at a specific point near the base of the iris to open the aqueous humor drainage channels of the eye. The goal is to mimic an effect of certain glaucoma medicines that achieve the same result by causing contraction of the ciliary muscle. Perfection of this embodiment will require description of the optimum design of the base end of the haptics that sit in the sulcus, and perhaps other embellishments so it may best to allude to it in case details distract from the AIOL functioning.

One or more embodiments of the present disclosure can provide a Haptic design that allows for post-operative adjustment of amplitude of IOLA by selective application of energy to its elements to alter their elasticity, tension, relative separation placement within the eye.

One or more embodiments of the present disclosure can provide a Haptic design that allows for post-operative adjustment of lens spherical and or toric power by selective application of energy to its elements to alter their elasticity, tension, relative separation placement within the eye. Embellishments made possible by selective application of energy to the haptics through dilated pupils include the ability to modify spherical power, the ability to modify toric power, and the ability to modify asphericity.

An optic design (either as a single optic design or one or both of a dual optic design) which can be incorporated into a single stage or modular IOL system and which can be part of an AIOL or conventional IOL in which the Haptic Passenger is an optic in the form of a flexible lens system having a periphery containing components that can expand or contract in response to selective application of energy, whose expansion and contraction alters the central curvature and thickness of the lens. Embellishments made possible by selective application of energy at the periphery of at least one of the optics through dilated pupils include the selective application of energy at the optic periphery can alter the optical properties of the lens optic by increasing the pinching action of rivet type supports connecting the anterior and posterior surfaces of an optic, separated by a viscolelastic fluid. This arrangement allowing post-operative treatment that allows modification of the following lens optical properties: spherical power, cylindrical (Toric) power and axis to correct astigmatism, and correction of irregular astigmatism and higher order optical aberrations.

There are a number of stanchion contact designs used to translate the mechanical forces generated by CBA into IOLA by enhancing optic movement contemplated by the present disclosure including various contact designs, rigidity changes and curvatures.

One or more embodiments of the present disclosure can provide a Haptic design that by virtue of allowing later attachment of the Haptic Passenger also allows for its own injection into the eye in the form of a helical strip. The flexible strip may be inserted into the eye using an instrument or injector and once injected into the eye forms a closed circular ring, forms a "C" shaped ring, or forms a 'C' shaped ring whose ends can be joined to form a closed circular ring.

One or more embodiments of the present disclosure can provide a Haptic design that by virtue of allowing later attachment of the Haptic Passenger also allows for its own insertion into the eye through a small incision in the form of a circle with at least four points of elastic articulation. This method of articulating the relatively rigid segments of the circle allows the Haptic to fit through a narrow incision whilst maintaining enough rigidity to be guided behind the iris and preventing excessive disruption of the space between the iris and the lens capsule.

Because of the anatomy of the ocular globe, a small corneal incision, if constructed in a step like fashion at the correct location with a special instrument, can be self-sealing so that the pressure of fluid within the eye will keep it closed until it heals. The upper limit to the length of such an incision is generally considered to be no more than about three millimeters. It can be desirable that an IOL optic be at least about five millimeters in diameter to focus light on the retina. A smaller optic could cause glare, reflections, and other troublesome symptoms. To span the diameter of the capsular bag or ciliary sulcus and desirably be suspend the optic in place, the distance between opposite ends of the haptics can be about nine millimeters (in the case of the sulcus) and about twelve millimeters (in the case of capsular bag placement). Any device that requires stable placement in the sulcus or capsular bag will likely be subject to these constraints. Therefore, any IOL, however complex or elegant in design, will have extremely limited utility unless it can be placed within the eye through a small incision and also meet the minimum size requirements of the optic and haptic diameters. Several other anatomical and physiological factors place practical constraints on intraocular device design. Embodiments of the present disclosure can meet these practical constraints and provide patentable utility.

In some embodiments, the intended haptic passenger can be a single optic IOL. The embodiment can be one piece. The embodiment can include a single ring member. The single ring member can be continuous. The mechanism of morphological change allowing for entry of the single ring member through small corneal incision can be limited by the incorporated IOL optic, which should be in the shape of a disc, plate or star that is folded. Fold configurations may be like a taco, roll, or concertina. Each fold method can use forceps or an injector cartridge. The enhanced mechanism for accurate stanchion placement once the embodiment is inside the eye can be a star-shaped profile of the haptic (a result of the ring member and stanchions), distinct rounded contact points defined by the base ends of the stanchions, with connections between the base ends presenting a rounded planar profile with intervening fenestrations to allow flexing of the haptic and the flow of intraocular fluids. The nature of the optics (the optical properties) can be adjustable after surgery.

In some embodiments, the intended haptic passenger can be a single optic IOL. The embodiment can be one piece. The embodiment can include more than one ring member. Each of the ring members can be continuous. The mechanism of morphological change allowing for entry of the single ring member through small corneal incision can be limited by the incorporated IOL optic, which should be in the shape of a disc, plate or star that is folded. Fold configurations may be like a taco, roll, or concertina. Each fold method can use forceps or an injector cartridge. The enhanced mechanism for accurate stanchion placement once the embodiment is inside the eye can be an uncoiling motion, such as could occur with the embodiment shown in FIG. 13. The nature of the optics can be adjustable after surgery. Optic rotation during CBA would defeat some of the modification utility (especially astigmatism adjustment) unless the embodiment when uncoiled was configured to allow movement of the optics without rotation.

In some embodiments, the intended haptic passenger can be a single optic IOL that is modular. The ring member and stanchions can be one component and the haptic passenger can be mounted on the ring member and stanchions after the ring member and stanchions have been positioned in the eye. The embodiment can include a single ring member that is continuous. The mechanism of morphological change allowing for entry of the single ring member and stanchions through small corneal incision can be uniform flexibility, where the ring member and stanchions are deformable and placed behind iris with forceps or injector and released to unfold into position. Alternatively, the mechanism of morphological change can be rigid arcs separated by hinges, defining a collapsible ring member. The nature of the optics can be adjustable after surgery.

In some embodiments, the intended haptic passenger can be a single optic IOL that is modular. The ring member and stanchions can be one component and the haptic passenger can be mounted on the ring member and stanchions after the ring member and stanchions have been positioned in the eye. The embodiment can include a single ring member and the single ring member can each be discontinuous. The mechanism of morphological change allowing for entry of the single ring member through small corneal incision can be the ring member being a horse shoe shape. The ring member can be at least partially elastic and flexible. One end of the ring member can be placed into the anterior chamber through the incision, guided behind dilated iris, and the trailing end can then be guided through incision in a horizontal "Fosbury flop" manner so that ring member only has to flex partially. Alternatively, the embodiment can be implanted with an injector cartridge. The at least partially-flexible ring member can be placed into a curved syringe-type injector. A plunger can be used to push the embodiment into the eye, which reforms its curve as its leading end is guided under the iris. The curve and rotation of the injector assists in laying down the embodiment into place. The injector tip can be rotated to allow placement with minimal trauma. The nature of the optics can be adjustable after surgery.

In some embodiments, the intended haptic passenger can be a single optic IOL that is modular. The ring member and stanchions can be one component and the haptic passenger can be mounted on the ring member and stanchions after the ring member and stanchions have been positioned in the eye. The embodiment can include more than one ring member and the ring members can each be continuous. The mechanism of morphological change allowing for entry of the ring members through a small corneal incision can be can be uniform flexibility, where the ring member and stanchions are deformable and placed behind iris with forceps or injector and released to unfold into position. The enhanced mechanism for accurate stanchion placement once the embodiment is inside the eye can be a star-shaped profile of the haptic (a result of the ring member and stanchions), distinct rounded contact points defined by the base ends of the stanchions, with connections between the base ends presenting a rounded planar profile with intervening fenestrations to allow flexing of the haptic and the flow of intraocular fluids. The enhanced mechanism for accurate stanchion placement once the embodiment is inside the eye can be an uncoiling motion, such as could occur with the embodiment shown in FIG. 13. Alternatively, the mechanism of morphological change can be rigid arcs separated by hinges, defining a collapsible ring member. The nature of the optics (the optical properties) can be adjustable after surgery. The nature of the optics can be adjustable after surgery.

In some embodiments, the intended haptic passenger can be a multi-optic IOL that is one-piece or modular. Such embodiments can include a single ring member or more than one ring members. The rings of a one-piece or modular embodiment can be continuous. For one-piece embodiments, the mechanism of morphological change allowing for entry of the single ring member through small corneal incision can be limited by the incorporated IOL optic, which should be in the shape of a disc, plate or star that is folded. Fold configurations may be like a taco, roll, or concertina. Each fold method can use forceps or an injector cartridge. The enhanced mechanism for accurate stanchion placement once the embodiment is inside the eye can be a star-shaped profile of the haptic (a result of the ring member and stanchions), distinct rounded contact points defined by the base ends of the stanchions, with connections between the base ends presenting a rounded planar profile with intervening fenestrations to allow flexing of the haptic and the flow of intraocular fluids. The enhanced mechanism for accurate stanchion placement once the embodiment is inside eye can also be an uncoiling motion, such as could occur with the embodiment shown in FIG. 13. The nature of the optics can be adjustable after surgery. Optic rotation during CBA would defeat some of the modification utility (especially astigmatism adjustment) unless the embodiment when uncoiled was configured to allow movement of the optics without rotation. The nature of the optics can be can be adjustable after surgery.

In some embodiments of the present disclosure, a plurality of stanchions can be interconnected with a ring member and the embodiment can omit a lens. Such an embodiment can be implanted in a patient's eye without a lens. Such an embodiment can be placed in the ciliary sulcus and thereby increase aqueous humor outflow by stretching open the trabecular meshwork. Such an embodiment, when placed in the ciliary sulcus, can also decrease aqueous humor production by ciliary body. Any of the structural embodiments of the present disclosure can be placed in the ciliary sulcus without a lens.

In another alternative embodiment, as shown in FIGS. 16-19, an accommodating intraocular lens assembly 10*j* can include a plurality of stanchions each extending between a base end and a distal end, such as stanchion 12*j* with base end 14*j* and distal end 16*j*. The embodiment of the present disclosure illustrated in FIGS. 16-19 can be viewed as a double ring embodiment capable of being coiled. The base ends can be disposed in spaced relation to one another about a first arcuate periphery 18*j* extending in a first plane. The distal ends can be disposed about a second arcuate periphery extending in a second plane. The first plane can be spaced from the second plane in a posterior direction along a central optic axis 26*j*. The first arcuate periphery can have a greater radius than the second arcuate periphery.

The accommodating intraocular lens assembly 10*j* can also include a ring member 46*j*. The ring member 46*j* can be interconnected with each of the plurality of distal ends 16*j*. The ring member 46*j* can include a disc portion 82*j* and a flange portion 84*j*. A haptic passenger such as a lens can be mounted on the ring member 46*j* after the ring member 46*j* and the stanchions 12*j* have been implanted in the eye.

The accommodating intraocular lens assembly 10*j* can also include a second plurality of stanchions each respectively extending between a second base end and a second distal end, such as stanchion 112*j* having base end 114*j* and distal end 116*j*. Each of the base ends of the second plurality of stanchions can be interconnected with one of the base ends of the first plurality of stanchions at intersections and thus be spaced from one another about the first arcuate periphery 18*j*. The second distal ends can be disposed about an arcuate periphery extending in a plane that is spaced from the plane of the second base ends along the central optic axis 26*j*. The first arcuate periphery 18*j* can have a greater radius than the arcuate periphery of the second distal ends.

The accommodating intraocular lens assembly 10*j* can also include a ring member 146*j*. The ring member 146*j* can be interconnected with each of the plurality of distal ends 116*j*. The ring member 146*j* can include a disc portion 182*j* and a flange portion 184*j*. The flange portion 184*j* can be positioned radially inward of the flange portion 84*j*. A haptic passenger such as a lens can be mounted on the ring member 146*j* after the ring member 146*j* and the stanchions 112*j* have been implanted in the eye.

Figure 16:
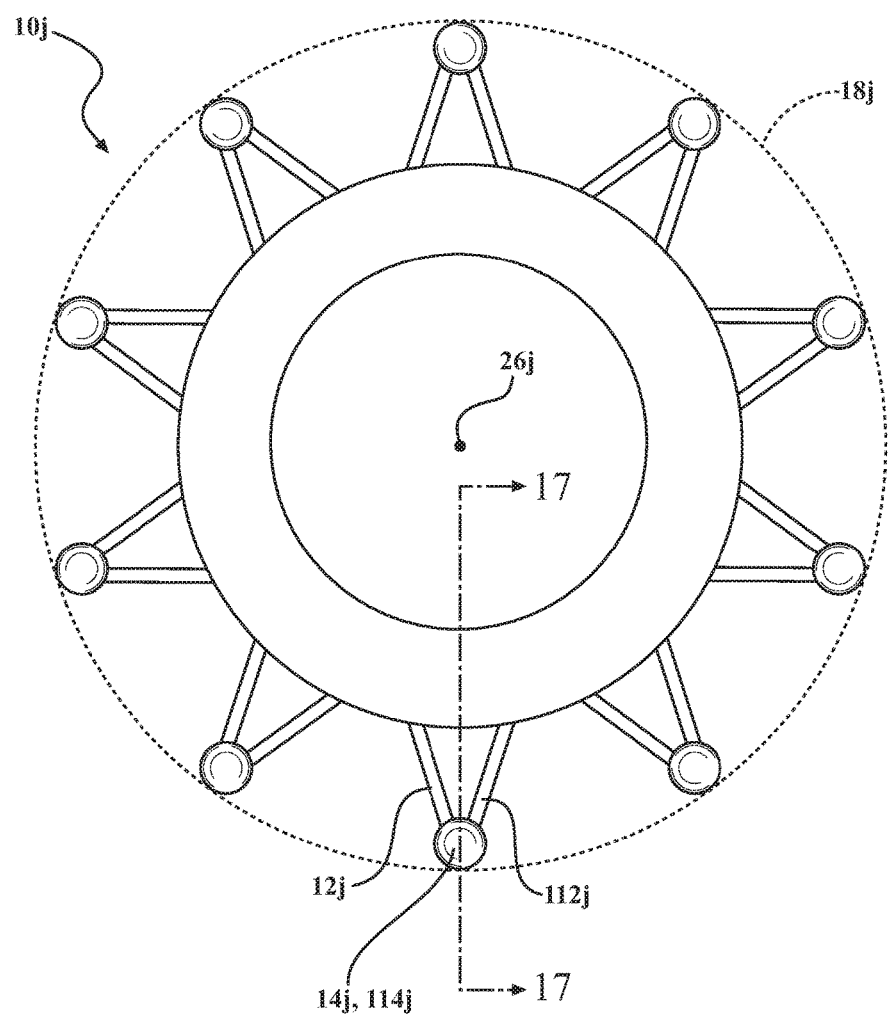
FIG. 16 is a top view of another exemplary embodiment of the present disclosure in an uncoiled configuration.

The stanchions 12*j* each extend along a first path transverse to and spaced from the central optic axis 26*j* in a first plane transverse the central optic axis 26*j*. FIG. 16 is a view of such a plane. Each of the second plurality of stanchions 112*j* extends along a second path that is transverse to and spaced from the central optic axis 26*j* in the first plane. The first path and the second path are mirrored with respect one another in a second plane containing the central optic axis 26*j*. This second plane is shown in FIG. 17.

Figure 17:
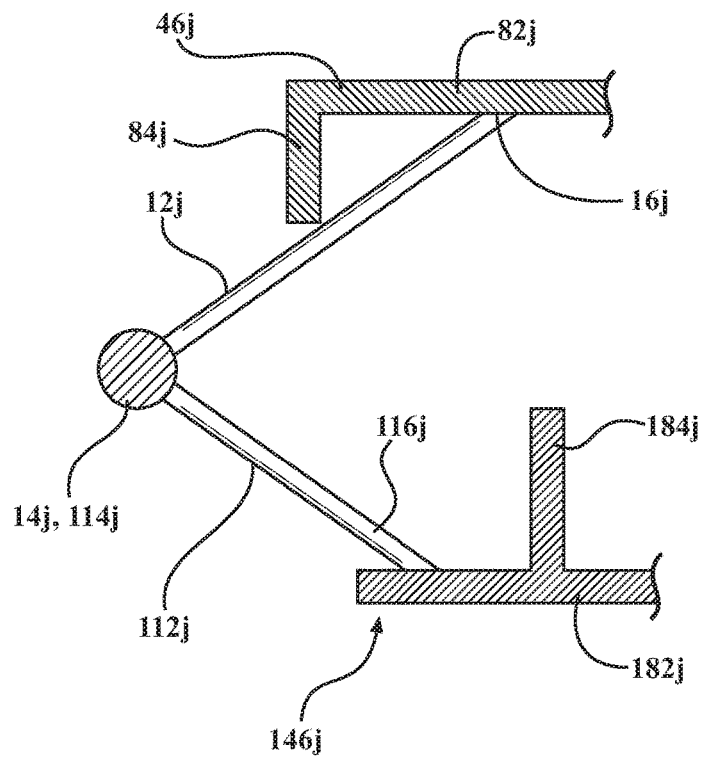
FIG. 17 is a cross-section taken at section lines 17-17 in FIG. 16.
Figure 18:
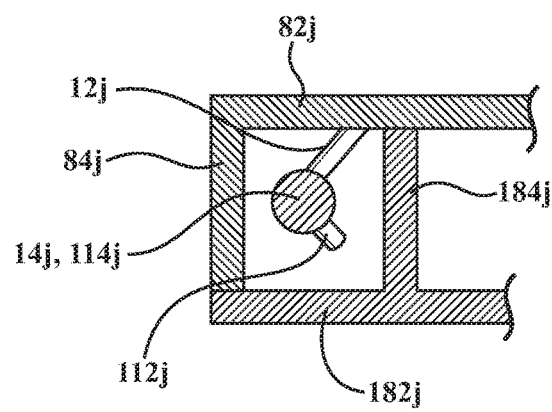
FIG. 18 is a cross-section analogous to FIG. 17 but of the embodiment in a coiled configuration.
Figure 19:
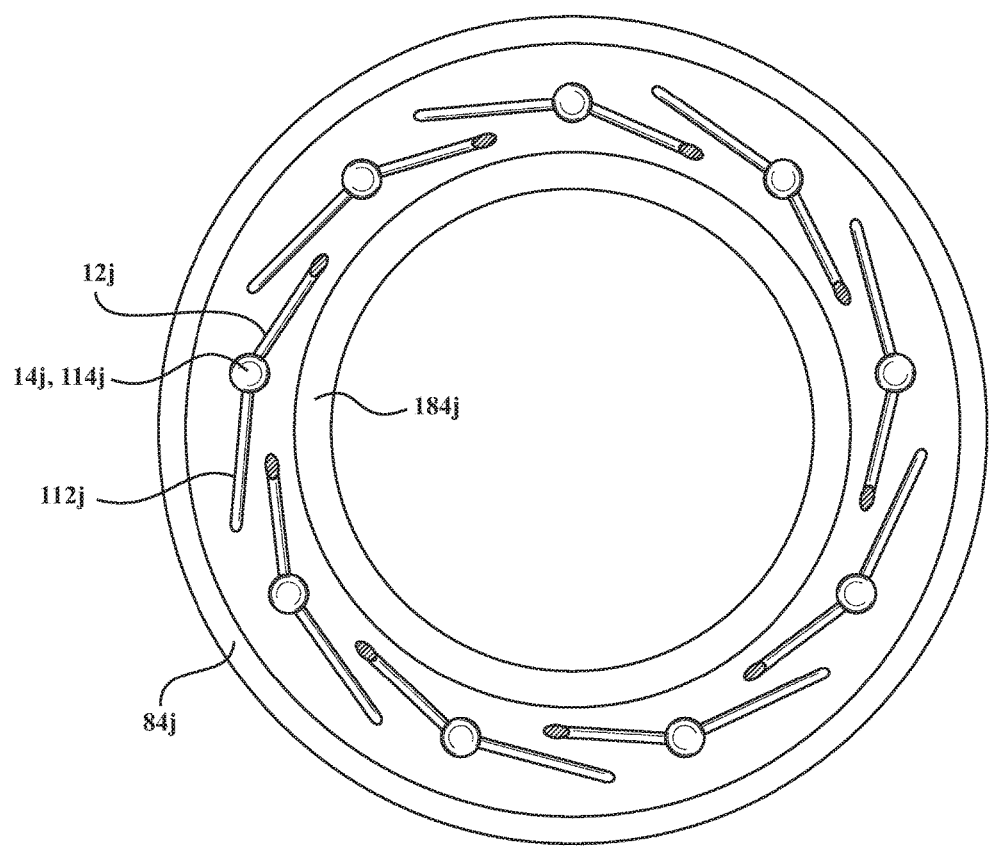
FIG. 19 is a top view of the embodiment shown in FIGS. 16-18, but of a top portion removed and in the coiled configuration.

FIGS. 16 and 17 show the alternative embodiment in an uncoiled configuration and FIGS. 18 and 19 show the alternative embodiment in an uncoiled configuration. The ring members 46*j* and 146*j* can be rotated relative to one another about the axis 26*j* to draw the stanchions 12*j*, 112*j* into an annular cavity defined by the ring members 46*j* and 146*j*. A radially inner boundary of the annular cavity can be defined by the flange portion 184*j*. A radially outer boundary of the annular cavity can be defined by the flange portion 84*j*. A posterior boundary of the annular cavity can be defined by the disc portion 82*j*. An anterior boundary of the annular cavity can be defined by the disc portion 182*j*. FIGS. 17 and 18 show the same cross-section; the embodiment 10*j* is shown in the uncoiled configuration in FIG. 17 and in the coiled configuration in FIG. 18. FIG. 19 is a view looking into the annular cavity with the disc portion 82*j* removed.

Figure 20:
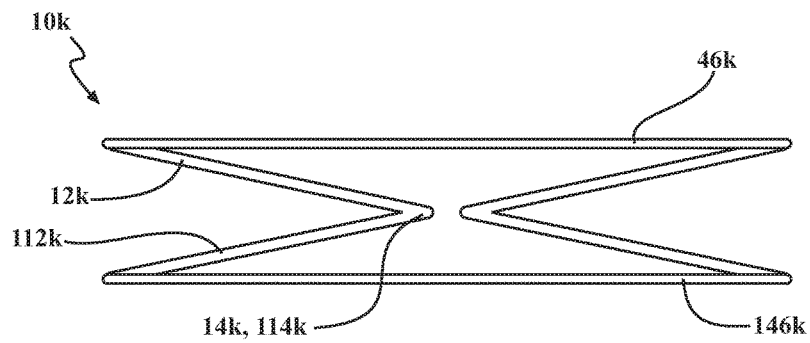
FIG. 20 is a schematic view of an embodiment in a pre-folded configuration.
Figure 21:
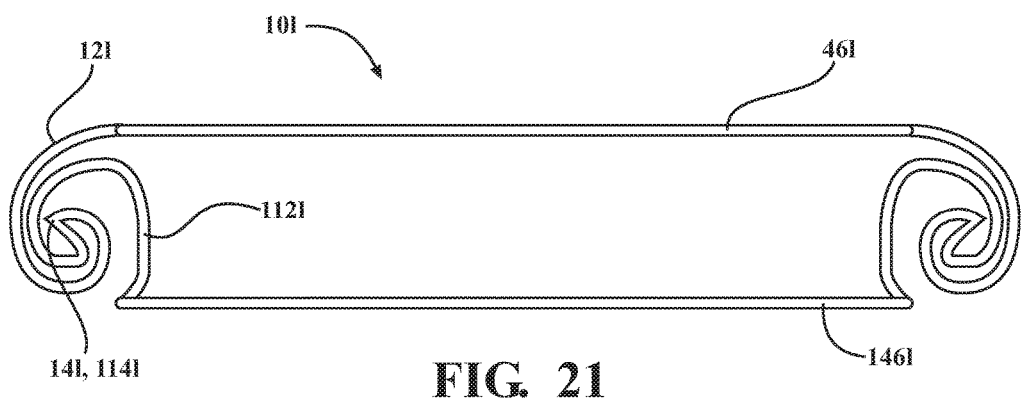
FIG. 21 is a schematic view of another embodiment in a pre-folded configuration.
Figure 22:
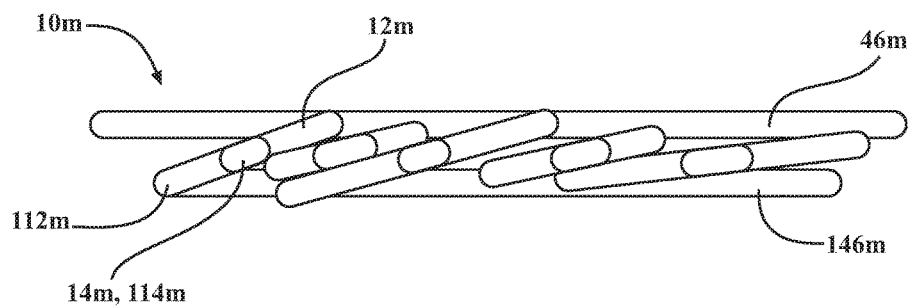
FIG. 22 is a schematic view of another embodiment in a pre-folded configuration.

FIGS. 20-22 are schematic views of various configurations in which an embodiment can be placed prior to folding and insertion in the eye of a patient. FIG. 20 shows an embodiment 10*k* with first and second ring members 46*k*, 146*k* and first and second sets of stanchions 12*k*, 112*k*. The stanchions 12*k*, 112*k* can be interconnected at a common base end 14*k*, 114*k*. Prior to folding, the stanchions 12*k*, 112*k* can be inverted, with the common base end 14*k*, 114*k* moved in between the first and second ring members 46*k*, 146*k*. The first and second ring members 46*k*, 146*k* can then be moved together, to the extent possible, and the entire structure can then be folded into a taco shell shape.

FIG. 21 is a schematic view of another embodiment in a pre-folded configuration. FIG. 21 shows an embodiment 10*l* with first and second ring members 46*l*, 146*l* and first and second sets of stanchions 12*l*, 112*l*. The stanchions 12*l*, 112*l* can be interconnected at a common base end 14*l*, 114*l*. Prior to folding, the stanchions 12*l*, 112*l* can be "rolled" together, with the common base end 14*k*, 114*k* at the center of the roll. The first and second ring members 46*k*, 146*k* can be rolled as well or can be moved together to the extent possible. The entire structure can then be folded into a taco shell shape.

FIG. 22 is a schematic view of another embodiment in a pre-folded configuration. FIG. 22 shows an embodiment 10*m* with first and second ring members 46*m*, 146*m* and first and second sets of stanchions 12*m*, 112*m*. The stanchions 12*m*, 12*m* can be interconnected at a common base end 14*m*, 114*m*. Prior to folding, the first and second ring members 46*m*, 146*m* can be rotated relative to one another and thereby drawing the first and second sets of stanchions 12*m*, 112*m* in between the first and second ring members 46*m*, 146*m*. The first and second ring members 46*m*, 146*m* can then be folded into a taco shell shape.

It is noted that additional claims that can asserted in a divisional patent application include:

A method of positioning an accommodating intraocular lens assembly in an eye comprising:

implanting an accommodating intraocular lens assembly having a positive power lens in the eye wherein the accommodating intraocular lens assembly also includes a plurality of stanchions each extending between the respective base end and a distal end, the plurality of base ends disposed in spaced relation to one another about a first arcuate periphery extending in a first plane wherein the first arcuate periphery is positioned in a ciliary sulcus of the eye, the distal ends disposed about a second arcuate periphery extending in a second plane positioned forward and outside of a capsular bag of the eye, the first plane spaced from the second plane in a posterior direction along a central optic axis, the first arcuate periphery having a greater radius than said second arcuate periphery and wherein the positive-power lens has an anterior side and a posterior side and a center disposed between the anterior side and the posterior side, the positive-power lens connected with each of the plurality of distal ends whereby a center of the positive power lens is moved along the central optic axis in response to contraction of the first arcuate periphery by contraction of the ciliary sulcus.

The method recited in paragraph [00202] wherein said implanting is further defined as:

implanting the accommodating intraocular lens assembly having the positive power lens in the eye wherein the accommodating intraocular lens assembly also includes a second plurality of stanchions each respectively extending between a second base end and a second distal end, each of the plurality of second base ends disposed in spaced relation to one another about said first arcuate periphery and are interconnected to one of said plurality of base ends at respective intersections positioned along said first arcuate periphery, the second distal ends disposed about a third arcuate periphery extending in a third plane, the third plane spaced from the first plane and the second plane along the central optic axis, the first arcuate periphery having a greater radius than the third arcuate periphery, and the accommodating intraocular lens assembly also including a secondary lens having a second anterior side and a second posterior side and a second center disposed between the second anterior side and the second posterior side, said second anterior side confronting the posterior side, the secondary lens connected with each of the second plurality of distal ends whereby the second center of the secondary lens is moved along the central optic axis in response to contraction of the first arcuate periphery by contraction of the ciliary sulcus.

The method recited in paragraph [00202] wherein said implanting is further comprising:

implanting a second plurality of stanchions the accommodating intraocular lens assembly in the ciliary sulcus, each of the second plurality of stanchions respectively extending between a second base end and a second distal end, each of the plurality of second base ends disposed in spaced relation to one another about a third arcuate periphery in a third plane spaced from the first plane along the central optic axis, the second distal ends disposed about a fourth arcuate periphery extending in a fourth plane, the fourth plane spaced from the third plane along the central optic axis, the third arcuate periphery having a greater radius than the fourth arcuate periphery, and the accommodating intraocular lens assembly also including a secondary lens having a second anterior side and a second posterior side and a second center disposed between the second anterior side and the second posterior side, said second anterior side confronting the posterior side, the secondary lens connected with each of the second plurality of distal ends whereby the second center of the secondary lens is moved along the central optic axis in response to contraction of the first arcuate periphery by contraction of the ciliary sulcus.

The method recited in paragraph [00202] further comprising:
filling at least one of the plurality of stanchions with fluid after said implanting.

The method recited in paragraph [00202] further comprising:
folding the accommodating intraocular lens assembly prior to said implanting.

The method recited in paragraph [00202] further comprising:
modifying at least one mechanical property of at least one of the plurality of stanchions after said implanting.

The method recited in paragraph [00212] wherein said modifying further comprises:
applying electromagnetic energy to a portion of the at least one of the plurality of stanchions and thereby modifying an elasticity of the at least one of the plurality of stanchions.

While the present disclosure has been described with reference to an exemplary embodiment, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the appended claims. The right to claim elements and/or sub-combinations that are disclosed herein as other present disclosures in other patent documents is hereby unconditionally reserved.

What is claimed is:

1. An accommodating intraocular lens assembly comprising:
a plurality of stanchions each extending between a base end and a distal end, said plurality of base ends disposed in spaced relation to one another about a first arcuate periphery extending in a first plane, said distal ends disposed about a second arcuate periphery extending in a second plane, said first plane spaced from said second plane in a posterior direction along a central optic axis, said first arcuate periphery having a greater radius than said second arcuate periphery;
a positive-power lens having an anterior side and a posterior side and a center disposed between said anterior side and said posterior side, said positive-power lens connected with each of said plurality of distal ends whereby said center of said positive power lens is moved anteriorly along said central optic axis in response to contraction of said first arcuate periphery; and
wherein at least one of said plurality of stanchions includes a first portion extending substantially straight from said positive-power lens toward said base end in a third plane containing said central optic axis and includes a second portion extending along an arcuate profile in said third plane, said arcuate profile defined by at least one radius and at least one center of curvature.

2. The accommodating intraocular lens assembly of claim 1 wherein at least one of said plurality of stanchions is further defined as configured to be adjustable after placement in an eye with laser energy.

3. The accommodating intraocular lens assembly of claim 1 wherein said at least one center of curvature is posterior of said base end along said central optic axis.

4. The accommodating intraocular lens assembly of claim 3 wherein said at least one center of curvature is between said base end and said distal end relative to a direction perpendicular to said central optic axis.

5. The accommodating intraocular lens assembly of claim 4 wherein said at least one center of curvature is closer to said base end than said distal end along said direction.

6. The accommodating intraocular lens assembly of claim 1 wherein said first arcuate periphery is configured for positioning in a ciliary sulcus, anteriorly of the ciliary muscle, and each of said plurality of stanchions extends away from said positive power lens in said posterior direction at an acute angle from one of the first plane and the second plane.

7. An accommodating intraocular lens assembly comprising:
a plurality of stanchions each extending between a base end and a distal end, said plurality of base ends disposed in spaced relation to one another about a first arcuate periphery extending in a first plane, said distal ends disposed about a second arcuate periphery extending in a second plane, said first plane spaced from said second plane in a posterior direction along a central optic axis, said first arcuate periphery having a greater radius than said second arcuate periphery; and
a positive-power lens having an anterior side and a posterior side and a center disposed between said anterior side and said posterior side, said positive-power lens connected with each of said plurality of distal ends whereby said center of said positive power lens is moved along said central optic axis in response to contraction of said first arcuate periphery; and
wherein said first arcuate periphery is configured for positioning in a ciliary sulcus, anteriorly of the ciliary muscle, and each of said plurality of stanchions extends away from said positive power lens in said posterior direction at an acute angle greater than twenty degrees and less than ninety degrees.

8. The accommodating intraocular lens assembly of claim 7 wherein at least one of said plurality of stanchions extends along an arcuate profile in a plane containing said central optic axis, said arcuate profile defined by at least one radius and at least one center of curvature.

9. The accommodating intraocular lens assembly of claim 7 wherein at least one of said plurality of stanchions is further defined as configured to be adjustable after placement in an eye with laser energy.

10. The accommodating intraocular lens assembly of claim 7 wherein at least one of said plurality of stanchions includes a first portion extending substantially straight from said positive-power lens toward said base end in a third plane containing said central optic axis and includes a second portion extending along an arcuate profile in said third plane, said arcuate profile defined by at least one radius and at least one center of curvature.

11. The accommodating intraocular lens assembly of claim 10 wherein said accommodating intraocular lens assembly is further defined as configured such that said at least one center of curvature is within zonules of the eye when said accommodating intraocular lens assembly is positioned in the eye and the ciliary muscle is relaxed.

12. The accommodating intraocular lens assembly of claim 10 wherein said accommodating intraocular lens assembly is further defined as configured such that said at least one center of curvature is outside of a capsular bag of the eye when said accommodating intraocular lens assembly is positioned in the eye and the ciliary muscle is relaxed.

13. An accommodating intraocular lens assembly comprising:
a plurality of stanchions each extending between a base end and a distal end, said plurality of base ends disposed in spaced relation to one another about a first arcuate periphery extending in a first plane, said distal ends disposed about a second arcuate periphery extending in a second plane, said first plane spaced from said second plane in a posterior direction along a central optic axis, said first arcuate periphery having a greater radius than said second arcuate periphery; and
a positive-power lens having an anterior side and a posterior side and a center disposed between said anterior side and said posterior side, said positive-power lens connected with each of said plurality of distal ends whereby said center of said positive power lens is moved anteriorly along said central optic axis in response to contraction of said first arcuate periphery;
a second plurality of stanchions each respectively extending between a second base end and a second distal end, each of said plurality of second base ends disposed in spaced relation to one another about a third arcuate periphery extending in a third plane, said second distal ends disposed about a fourth arcuate periphery extending in a fourth plane, said third plane spaced from said fourth plane along said central optic axis, said third arcuate periphery having a greater radius than said fourth arcuate periphery; and
a secondary lens having a second anterior side and a second posterior side and a second center disposed between said second anterior side and said second posterior side, second anterior side confronting said posterior side, said secondary lens connected with each of said plurality of second distal ends whereby said second center of said secondary lens is moved along said central optic axis in response to contraction of said third periphery, and said secondary lens spaced from said positive power lens.

14. The accommodating intraocular lens assembly of claim 13 wherein at least one of said plurality of stanchions and said second plurality of stanchions extends along said a plurality of arcuate profiles in a fifth plane containing said central optic axis, said arcuate profiles defined by more than one radius or more than one center of curvature in said fifth plane and separated by a straight section of said at least one of said plurality of stanchions and said second plurality of stanchions.

15. The accommodating intraocular lens assembly of claim 13 wherein at least some of said plurality of second base ends are interconnected to some of said plurality of base ends at respective intersections positioned along said first arcuate periphery such that said first arcuate periphery and said third arcuate periphery are coplanar and wherein an acute angle is defined between at least one of said plurality of stanchions and at least one of said plurality of second stanchions extending away from one of said intersection of said base end and said second base end.

16. The accommodating intraocular lens assembly of claim 13 wherein
at least one of said plurality of stanchions extends along a first arcuate profile in a plane containing said central optic axis, said first arcuate profile defined by at least one first radius and at least one first center of curvature;
at least one of said second plurality of stanchions extends along a second arcuate profile in said plane containing said central optic axis, said second arcuate profile defined by at least one second radius and at least one second center of curvature, said first radius different than said second radius or said first center of curvature different than said second center of curvature; and
said at least one of said plurality of stanchions and said at least one of said second plurality of stanchions extend away from said respective base end and second base end in the same direction along said central optic axis.

17. The accommodating intraocular lens assembly of claim 13 wherein at least some of said plurality of second base ends are interconnected to some of said plurality of base ends at respective intersections positioned along said first arcuate periphery such that said first arcuate periphery and said third arcuate periphery are coplanar and wherein a thickness of said intersection of said base end and said second base end is greater than a combination of a thickness of a stanchion of said plurality of stanchions extending from said intersection and a thickness of a stanchion of said second plurality of stanchions extending from said intersection.

18. The accommodating intraocular lens assembly of claim 13 wherein at least one of said second plurality of stanchions extends along a plurality of arcuate profiles in a fifth plane containing said central optic axis, said arcuate profiles defined by more than one radius or more than one center of curvature in said fifth plane and wherein a first of said centers of curvature is positioned on an anterior side of said at least one of said second plurality of stanchions and a second of said centers of curvature is positioned on a posterior side of said at least one of said second plurality of stanchions.

19. The accommodating intraocular lens assembly of claim 13 wherein at least one of said plurality of stanchions and said second plurality of stanchions is further defined as configured to be adjustable after placement in an eye with laser energy.

20. The accommodating intraocular lens assembly of claim 13 wherein said first arcuate periphery and said third arcuate periphery are configured for positioning in a ciliary sulcus, anteriorly of the ciliary muscle.

* * * * *